US005710234A

United States Patent [19]
Fujishiro et al.

[11] Patent Number: 5,710,234
[45] Date of Patent: Jan. 20, 1998

[54] ORTHO SPIROESTERS AND CURABLE AND CURED RESIN COMPOSITIONS OF SAME

[75] Inventors: Koichi Fujishiro; Masaya Furukawa; Kazuhiro Watanabe; Takero Teramoto, all of Kawasaki, Japan

[73] Assignees: Nippon Steel Chemical Co., Ltd.; Nippon Steel Corporation, both of Tokyo, Japan

[21] Appl. No.: 583,055

[22] PCT Filed: Jul. 19, 1994

[86] PCT No.: PCT/JP94/01189

§ 371 Date: Jan. 19, 1996

§ 102(e) Date: Jan. 19, 1996

[87] PCT Pub. No.: WO95/03310

PCT Pub. Date: Feb. 2, 1995

[30] Foreign Application Priority Data

| Jul. 20, 1993 | [JP] | Japan | 5-179131 |
| Aug. 30, 1993 | [JP] | Japan | 5-214292 |
| Aug. 30, 1993 | [JP] | Japan | 5-214293 |

[51] Int. Cl.$^6$ ............ C08G 59/40; C08G 65/00; C08G 63/08

[52] U.S. Cl. ............ 528/106; 528/112; 528/297; 528/354; 528/355

[58] Field of Search ............ 528/97, 106, 112, 528/297, 354, 355; 575/533

[56] References Cited

U.S. PATENT DOCUMENTS

| 4,368,314 | 1/1983 | Endo et al. | 525/507 |
| 4,574,132 | 3/1986 | Sayles | 523/466 |
| 4,707,534 | 11/1987 | Schult | 528/97 |
| 4,738,899 | 4/1988 | Bluestein et al. | 428/413 |
| 5,369,192 | 11/1994 | Ko et al. | 525/484 |

FOREIGN PATENT DOCUMENTS

| 56-40329 | 9/1981 | Japan . |
| 58-57423 | 12/1983 | Japan . |
| 61-243869 | 10/1986 | Japan . |
| 61-264016 | 11/1986 | Japan . |
| 63-17908 | 1/1988 | Japan . |
| 2-073823 | 3/1990 | Japan . |
| 2-116851 | 5/1990 | Japan . |
| 2-117913 | 5/1990 | Japan . |
| 2-247654 | 10/1990 | Japan . |
| 2-274720 | 11/1990 | Japan . |
| 4-340965 | 11/1992 | Japan . |
| 4-345608 | 12/1992 | Japan . |
| 4-363311 | 12/1992 | Japan . |
| 5-009264 | 1/1993 | Japan . |
| 5-148411 | 6/1993 | Japan . |

*Primary Examiner*—James J. Seidleck
*Assistant Examiner*—Randy Gulakowski
*Attorney, Agent, or Firm*—Birch, Stewart, Kolasch & Birch, LLP

[57] ABSTRACT

Ortho spiroesters of excellent heat resistance and low volume shrinkage during curing are disclosed. Resin compositions of excellent heat resistance and low curing shrinkage containing these ortho spiroesters are also provided. These photosensitive or heat-curable resin compositions are formulated from photo- or heat-polymerizable compounds containing ethylenic double bonds and carboxyl groups, photopolymerization initiators and sensitizers, or polymerization initiators which generate radicals by heat, and said ortho spiroesters. These resin compositions have low curing shrinkage and are useful for applications requiring dimensional accuracy such as molding materials, encapsulants, adhesives and coatings and also for the preparation of image-forming materials such as protective films for color filters, inks and electrically insulating spacers for touch panels.

6 Claims, 4 Drawing Sheets

ORTHO SPIROESTERS AND CURABLE AND CURED RESIN COMPOSITIONS OF SAME

TECHNICAL FIELD

This invention relates to novel ortho spiroesters useful for formulating a resin composition which cures with either low shrinkage or expansion during molding and to a resin composition of low curing shrinkage containing said ortho spiroesters and a cured product of said composition.

BACKGROUND TECHNOLOGY

In general, thermosetting resins such as epoxy resins, unsaturated polyesters and polyfunctional (meth)acrylic resins cure invariably with shrinkage and this leads to cracking and poor appearance by internal stress. Even epoxy resins, known to cure with the least shrinkage among a variety of thermosetting resins, undergo a volume shrinkage on the order of 3 to 6% and thereby pose a number of problems.

Remedial measures hitherto adopted are, for example, an addition of inorganic fillers such as silica, calcium carbonate and alumina to lower the degree of curing shrinkage on a relative scale. The resin compositions in question, however, increase in viscosity as a result of the addition of fillers and become difficult to cast at low temperature.

Attempts have been made to prevent volume shrinkage by adding resins that are inert and miscible with epoxy resins to epoxy resins as disclosed in Japan Tokkyo Koho No. Sho 58-57,423 (1983). This approach, however, is not desirable as it often tends to deteriorate the properties, particularly the heat resistance, of cured resins.

Apart from the aforementioned attempts, studies are in progress to reduce the degree of shrinkage by modifying resins alone. For example, 1,4,6-trioxaspiro(4,4)nonane which is prepared by the reaction of ethylene oxide with γ-butyrolactone is known as a monomer that undergoes no shrinkage during polymerization [Kobunshi, 27, 108 (1978) and elsewhere]. Polymers obtained by ring-closing polymerization of this compound are thermoplastic, but they could become thermosetting when the compound is made bifunctional [J. Macromol. Sci., Chem., A9, 849 (1975); J. Polym. Sci., Polym. Shimp., 56, 117 (1976)].

According to the aforementioned scheme, ortho spiroesters containing a hydroquinone or 2,2-bis(4-hydroxyphenyl)propan skeleton are ring-opened and cured at room temperature for 24 hours in the presence of boron trifluoride-diethyl ether complex as a catalyst. This procedure can reduce the shrinkage substantially to zero during curing.

Ortho spiroesters, however, are solids or highly viscous liquids at room temperature and, in commercial uses as casting materials or adhesives, they are often mixed with diluents of larger curing shrinkage. Ortho spiroesters, however, are known to cure with lower heat resistance than epoxy resins. Hence, they cannot be used in high proportions in the cases where they are used in admixture with diluents of larger curing shrinkage in applications requiring high heat resistance.

Screen printing has been used widely in the conventional patterning. This technique, however, generates such phenomena as bleeding and smudging and is finding it difficult to cope with the trend for higher density and accuracy in patterning. To solve this problem, patterning by dispense of resist formulations based on photosensitive resins is drawing attention. Resists of this kind are, for example, dry-film photoresists and liquid developable resist inks.

Dry-film photoresists, however, tend to trap air bubbles during lamination under heat and also leave some uncertainty about heat resistance and adhesive properties. Besides, they are expensive.

On the other hand, liquid resists are tacky after cure and cause soiling of masks. In consequence, liquid resists are not amenable to a procedure of close-contact exposure which contributes to higher resolution and is advantageous to tapering. Furthermore, liquid photoresists currently available on the market use organic solvents as developing solutions and these solvents are potential air pollutants and also expensive. For example, Japan Kokai Tokkyo Koho No. Sho 61-243,869 (1986) discloses photosensitive resin compositions which are mainly composed of phenol novolak resins and can be developed with a weakly alkaline aqueous solution. The compositions in question, however, suffered loss of their adhesive strength to substrates after curing on account of a high crosslinking density and, in actual application, encountered a problem of coming off of spacers.

Photopolymerizable compounds, for example adducts of epoxy (meth)acrylates with acid anhydrides and adducts of copolymers of maleic anhydride and vinyl compounds with hydroxyl group-containing (meth)acrylate esters, are disclosed as alkali-developable photosensitive resins in Japan Tokkyo Koho No. Sho 56-40,329 (1981) and Japan Kokai Tokkyo Koho Nos. Sho 63-17,908 (1988), Hei 4-345,608 (1992), Hei 4-340,965 (1992), and Hei 2-247,654 (1990).

The aforementioned alkali-developable photosensitive resins normally show a large curing shrinkage of 4% or more and form films of poor adhesiveness and moisture resistance by photocuring alone. In consequence, efforts are being made to improve the properties such as moisture resistance and alkali resistance by formulating compositions from the said photosensitive compounds and epoxy resins, carrying out photocure, development and thermal cure and allowing the epoxy groups to react with the carboxyl groups present in the photosensitive compounds. Epoxy resins, however, cure with some shrinkage as mentioned earlier and the problems of residual internal stress and cracking still remain.

One attempt to remedy the aforementioned defects has been an addition of inorganic fillers such as silica, calcium carbonate and alumina to effect relative reduction of curing shrinkage. The addition of fillers, however, raises the viscosity of a resin composition and poses another problem, that is, it makes casting of the composition difficult at low temperature. Moreover, this scheme is not applicable to the cases where the cured products need to be transparent.

Another attempt to prevent volume shrinkage is an addition to epoxy resins of those resins which are inert and miscible with said epoxy resins as disclosed in Japan Tokkyo Koho No. Sho 58-57,423 (1983). This process, however, is undesirable as it often causes the resins to cure with deterioration of their properties, in particular, of the heat resistance.

Although the use of the aforementioned alkali-developable photosensitive resins as raw materials in the manufacture of color filters is disclosed as a concrete example of their applications, there still remain unsolved the problems of tack after precure, large shrinkage after postcure, decrease in thickness of protective films, dimensional decrease of patterns of color filters and generation of cracks.

A further use of said photosensitive resins as spacers in the form of electrically insulating separators for touch panels is conceivable though not referred to in the aforementioned prior art. It is to be noted, however, that the same problems as above regarding the application to color filters are present here.

An object of this invention is to provide novel ortho spiroesters which show excellent heat resistance and undergo large volume expansion during curing.

A second object of this invention is to provide a resin composition which contains novel ortho spiroesters, shows excellent heat resistance and undergoes low shrinkage during curing.

A third object of this invention is to provide a resin composition which is photosensitive and undergoes low shrinkage during curing by utilizing the alkali developability and heat resistance of carboxyl group-containing photopolymerizable compounds and adding ortho spiroesters as constituent of said resin composition.

A fourth object of this invention is to provide a resin composition which is thermosetting and undergoes low shrinkage during curing by utilizing the heat resistance of cured products of thermally polymerizable compounds containing ethylenic double bonds and carboxyl groups and adding ortho spiroesters as constituent of said resin composition.

A fifth object of this invention is to provide cured products of the aforementioned resin compositions of low curing shrinkage.

A sixth object of this invention is to provide resin compositions of low curing shrinkage which show excellent dimensional stability and low residual stress and optical deformation when used as moldings, show excellent dimensional stability and adhesive strength when used as adhesives and form films of excellent adhesive strength and small decrease in film thickness when used as coatings.

A seventh object of this invention is to provide a resin composition of low curing shrinkage which is useful for patterning by resists with minimized decrease in pattern width after postbake when used as coating.

An eighth object of this invention is to provide a resin composition of low curing shrinkage useful for the following applications; coatings for insulating films, adhesives, precision casting materials, printing inks and coatings, in particular, protective films for color filters in liquid-crystal display devices and photographing devices; inks for color filters; color filters composed of said inks; and spacers as electrically insulating separators in touch panels for input of information installed in the upper part of a liquid display panel and touch panels composed of said spacers.

DISCLOSURE OF THE INVENTION

Firstly, this invention relates to ortho spiroesters represented by the following general formula (1)

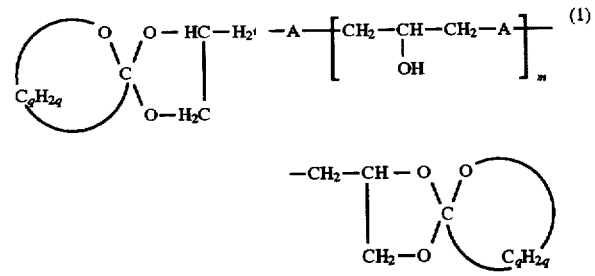

(wherein A is

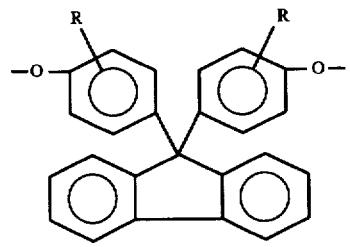

with R designating hydrogen or a lower alkyl group, m is 0 to 10 and q is an integer from 2 to 10).

Secondly, this invention relates to a resin composition of excellent heat resistance and low curing shrinkage containing the ortho spiroesters (a) represented by the aforementioned general formula (1) and to a cured product of said composition.

The ortho spiroesters represented by the aforementioned general formula (1) are novel compounds and they can be prepared by the addition reaction of diglycidyl ethers represented by the following general formula (2) (wherein h and m are the same as defined above) with lactones in the presence of a Friedel-Crafts catalyst such as boron trifluoride and boron trifluoride-diethyl ether complex or an acidic catalyst.

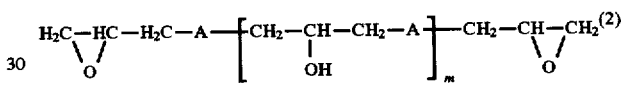

The lactones useful for the aforementioned reaction include β-propiolactone, γ-butyrolactone, γ-methylbutyrolactone, γ, γ-dimethylbutyrolactone, γ-valerolactone, δ-valerolactone and ε-caprolactone and preferable among them are γ-butyrolactone, γ-methylbutyrolactone and ε-caprolactone. The diglycidyl ethers useful for the reaction are those represented by the general formula (2) and A in (2) is the same as A in the general formula (1) and R is hydrogen or a lower alkyl group. Examples of the lower alkyl group are methyl, ethyl and isopropyl. The subscript m here is the same as m in the general formula (1) The aforementioned lactones may be used together with a small amount of lactones with substituents other than alkyl group, for example, α-chlorobutyrolactone.

The ortho spiroesters of this invention are represented by the aforementioned general formula (1) wherein m is 0 to 10. When used together with diluents, ortho spiroesters with m of greater than 10 show poorer miscibility with diluents and cure nonuniformly with a possible occurrence of cracking. It is not necessary for m to be a single number and a mixture of compounds with different m may be used. In the latter case, it is preferable for the average of m to be in the range of 0 to 10.

It is desirable form to be 0 to 3 in the majority, preferably 0 in 50% or more, of ortho spiroesters of this invention because such compounds give solutions or melts of lower viscosity.

The rings composed of [C, O, $C_qH_{2q}$] and present at both ends of the ortho spiroesters of the general formula (1) are preferably four- to seven-membered from the standpoint of curing rate and heat resistance of cured products.

The ortho spiroesters in question yield resin compositions of low curing shrinkage when used together with curing agents selected from organic polybasic acids and phenols or curing accelerators or a combination of the two.

Resin compositions containing the aforementioned ortho spiroesters are composition ① of low curing shrinkage which contains the following (a) and (b) and/or (c) as its components or composition ② of low curing shrinkage which contains the following (a), (d) and (b) and/or (c) as its components:

(a) ortho spiroesters of the aforementioned general formula (1),
(b) curing agents based on organic polybasic acids or phenols,
(c) curing accelerators, and
(d) oxirane group-containing epoxy resins.

The curing agents (b) based on organic polybasic acids act as curing agents for the ortho spiroesters and aromatic and alicyclic polybasic acids or their anhydrides are suitable as such; for example, benzophenonetetracarb oxylic acid anhydride, pyromellitic anhydride, trimellitic anhydride, phthalic anhydride, methylnadic anhydride, hexahydrophthalic anhydride and methylhexahydrophthalic anhydride. These curing agents may be used singly or as a mixture of two or more.

The curing agents (b) based on phenols are resins containing phenolic hydroxyl groups; for example, poly (vinylphenol), poly(halogenated vinyl phenol) and naphthol resins can be used as such curing agents. Usual phenolic resins can also be used; for example, novolak phenolic resins and resol phenolic resins which are prepared from phenol, ortho-cresol, para-cresol, para-ethylphenol, para-tert-butylphenol, para-sec-butylphenol, para-n-butylphenol, para-cyclohexylphenol, para-octylphenol, para-benzylphenol or bisphenol A and modifications of these phenolic resins. They can be used singly or as a mixture of two or more.

There is no restriction placed on the curing accelerators (c) and a variety of tertiary amine salts, imidazole salts, Lewis acids and Broensted acids can be used.

The oxirane group-containing epoxy resins (d) are not limited to any specific epoxy resins and preferable examples are bisphenol A-based epoxy resins, bisphenol F-based epoxy resins, phenol novolak epoxy resins, cresol novolak epoxy resins, alicyclic epoxy resins and heterocyclic compound-based epoxy resins. They are used singly or as a mixture of two or more. It is not advantageous to use epoxy resins represented by the general formula (2) alone as component (d).

In the case of the aforementioned resin composition ① of low curing shrinkage containing (a) and (b) and/or (c), the composition is formulated from 100 parts by weight of the component (a), 50 to 150 parts by weight of the component (b) and 0.01 to 10 parts by weight of the component (c). The presence of either or both of (b) and (c) suffices in this case.

In the case of the aforementioned resin composition ② of low curing shrinkage containing (a), (d) and (b) and/or (c), the ratio by weight of (a) to (d) is preferably chosen so that (a)/(d) lies in the range of 10/90 to 70/30 while the ratios of (b) to (a) and (c) to (a) are chosen roughly the same as in the aforementioned composition ①. Likewise, the presence of either or both of (b) and (c) suffices here.

These resin compositions of low curing shrinkage are cured normally in the range of ambient temperature to 200° C. although the curing conditions vary with the kind and quantity of curing agents and curing accelerators.

Incorporation of the epoxy resins (d) in the formulation produces beneficial effects of reduced viscosity and improved heat resistance but somewhat adversely affects the effect of the ortho spiroesters (a) for lowering curing shrinkage. Thus, the proportion of (d) is determined according to the end use.

These resin compositions of low curing shrinkage cure with the formation of a network of ester linkages and yield thermosetting resins of excellent heat resistance.

It is possible to add, as needed, to the resin compositions of low curing shrinkage of this invention such additives as flexibilizers, fillers, dyes and pigments; for example, alkylphenol monoglycidyl ethers as flexibilizer and glass fibers, silica powders or boron nitride as filler.

The ortho spiroesters of this invention, when cured in the presence of curing agents, undergo large expansion in volume and their use facilitates the preparation of resin compositions curable with low volume shrinkage. The simultaneous use of the ortho spiroesters and epoxy resins helps to improve further the heat resistance.

Secondly, this invention relates to a photosensitive or heat-curable resin composition of low curing shrinkage which contains 100 parts by weight of (A) photo- or heat-polymerizable compounds containing ethylchic double bonds and carboxyl groups, 0.1 to 30 parts by weight of (B) photopolymerization initiators or sensitizers or 0.1 to 10 parts by weight of (B) polymerization initiators which generate radicals under heat (radical polymerization initiators) and 5 to 100 parts by weight of (C) ortho spiroesters represented by the following general formula (3) (wherein p is an integer from 3 to 5) containing two or more ortho spiroester groups and to a cured product obtained by curing said photosensitive or heat-curable resin composition of low curing shrinkage.

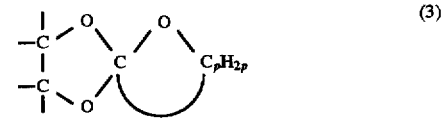
(3)

In this invention, a concrete example of the component A containing ethylenic double bonds and carboxyl groups is addition products of epoxy (meth)acrylates and acid anhydrides; they are prepared by the reaction of epoxy compounds with (meth)acrylic acid (which is a generic term hereinafter used to designate acrylic acid and methacrylic acid) to yield epoxy (meth)acrylates followed by the reaction of the hydroxyl groups in the epoxy (meth)acrylates with acid anhydrides.

Epoxy compounds useful for this reaction are represented by the general formula $Ar(OG)_n$ (wherein Ar is an aromatic group of n valence, G is glycidyl group and n is an integer of 2 or more, preferably 2).

Aromatic epoxy compounds such as above are provided by phenols, preferably by the following phenols: bis(4-hydroxyphenyl)ketone, bis(4-hydroxy-3,-dimethylphenyl) ketone, bis(4-hydroxy-3,5-dichlorophenyl)ketone, bis(4-hydroxyphenyl)sulfone, bis(4-hydroxy-3,5-dimethylphenyl) sulfone, bis(4-hydroxy-3,5-dichlorophenyl)sulfone, bis(4-hydroxyphenyl)hexafluoropropane, bis(4-hydroxy-3,5-dimethylphenyl)hexafluoropropane, bis(4-hydroxy-3,5-dichlorophenyl)hexafluoropropane, bis(4-hydroxyphenyl) dimethylsilane, bis(4-hydroxy-3,-dimethylphenyl) dimethylsilane, bis(4-hydroxy-3,5-dichlorophenyl) dimethylsilane, bis(4-hydroxyphenyl)methane, bis(4-hydroxy-3,5-dichlorophenyl)methane, bis(4-hydroxy-3,5-dibromophenyl)methane, 2,2-bis(4-hydroxyphenyl) propane, 2,2-bis(4-hydroxy-3,5-dimethylphenyl)propane, 2,2-bis(4-hydroxy-3,5-dichlorophenyl)propane, 2,2-bis(4-hydroxy-3-methylphenyl)propane, 2,2-bis(4-hydroxy-3-chlorophenyl)propane, bis(4-hydroxyphenyl)ether, bis(4-hydroxy-3,5-dimethylphenyl)ether and bis(4-hydroxy-3,5-dichlorophenyl)ether. Also useful are epoxy resins derived from phenols containing the skeleton of

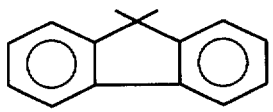

such as 9,9-bis(4-hydroxyphenyl)fluorene, 9,9-bis(4-hydroxy-3-methylphenyl)fluorene, 9,9-bis(4-hydroxy-3-chlorophenyl)fluorene, 9,9-bis(4-hydroxy-3-bromophenyl) fluorene, 9,9-bis(4-hydroxy-3-fluorophenyl)fluorene, 9,9-bis(4-hydroxy-3-methoxyphenyl)fluorene, 9,9-bis(4-hydroxy-3,5-dimethylphenyl)fluorene, 9,-bis(4-hydroxy-3,5-dichlorophenyl)fluorene, and 9,9-bis(4-hydroxy-3,5-dibromophenyl)fluorene or from 4,4'-biphenol and 3,3'-biphenol. Epoxy compounds are obtained by treating the aforementioned bisphenols with epichlorohydrin.

In addition to the aforementioned epoxy compounds, the following epoxy compounds can be used; phenol novolak epoxy resins, cresol novolak epoxy resins, polycarboxylic acid glycidyl esters, polyol polyglycidyl ethers, aliphatic or alicyclic epoxy resins and amine epoxy resins. Contamination with oligomers occurs during the etherification for introduction of glycidyl groups but this does not affect the performance of the resin compositions of low curing shrinkage of this invention.

Polybasic acids or their anhydrides reactive with the hydroxyl groups in epoxy (meth)acrylates include maleic anhydride, succinic anhydride, itaconic anhydride, phthalic anhydride, tetrahydrophthalic anhydride, hexahydrophthalic anhydride, methylendomethylenetetrahydrophthalic anhydride, chlorendic anhydride, methyltetrahydrophthalic anhydride, trimellitic anhydride, pyromellitic anhydride, benzophenonetetracarboxylic acid dianhydride, biphenyltetracarboxylic acid dianhydride, diphenyl ether tetracarboxylic acid dianhydride and other aromatic polycarboxylic acid anhydrides.

The component A containing ethylenic double bonds and carboxyl groups is not necessarily limited to the aforementioned compounds and the acceptable compounds may be used singly or as a mixture.

In view of the miscibility with the component C to be described later, the compounds preferable for the component A are those obtained by the reaction of epoxy compounds with (meth)acrylic acid followed by the reaction of the resulting epoxy (meth)acrylates with polybasic acids or their anhydrides. The presence of acid dianhydrides as polybasic acid anhydride in this reaction improves the developability with alkali when the product is formulated into a photosensitive resin composition of low curing shrinkage or improves the heat resistance when formulated into a heat-curable resin composition of low curing shrinkage.

The compounds described immediately above have main structural units represented by the following general formulas (4) and (5) [wherein $R_1$ and $R_2$ are hydrogen, alkyl group with 1 to 5 carbon atoms or halogen, $R_3$ is hydrogen or methyl group, X is —CO—, —SO$_2$—, —C(CF$_3$)$_2$—, —Si(CH$_3$)$_2$—, —CH$_2$—, —O—,

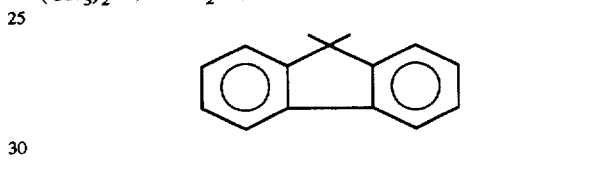

or nil, Y is the residue of acid anhydride, Z is the residue of acid dianhydride, t is an integer and either 0 or 1 and m:n is mol ratio of structural units in the range of 0/100 to 100/0].

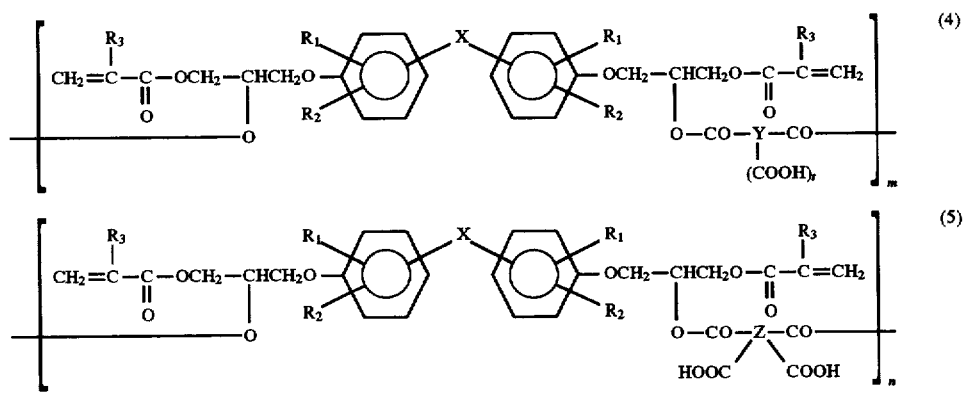

Other examples of the component A are compounds which are obtained by half-esterifying the maleic anhydride portion of the copolymers of maleic anhydride and monomers such as ethylene, propylene, isobutene, styrene, vinylphenol or its ethers or esters, acrylic acid, acrylate esters and acrylamide with alcoholic hydroxyl group-containing acrylates such as hydroxyethyl acrylate or epoxy group-containing acrylates such as glycidyl methacrylate and compounds which are obtained by treating the hydroxyl groups in the copolymers of (meth)acrylic acid or (meth)acrylate ester and alcoholic hydroxyl group-containing acrylates such as hydroxyethyl acrylate with (meth)acrylic acid.

Concrete examples of epoxy compounds capable of forming the compounds of the general formulas (4) and (5) are the aforementioned aromatic epoxy compounds derived from a variety of bisphenols, phenol novolaks and cresol novolaks and containing two or more epoxy groups in the molecule. In consequence of this derivation, the compounds with the main structural units of the general formulas (4) and (5) are bound to contain in part the following oligomers but this does not affect at all the resin compositions of low curing shrinkage of this invention. In the formula of the oligomers, B is a group derived from polybasic acid and r is an integer of 1 to 10, and the oligomers become identical with compounds of the formulas (4) and (5) when r=0.

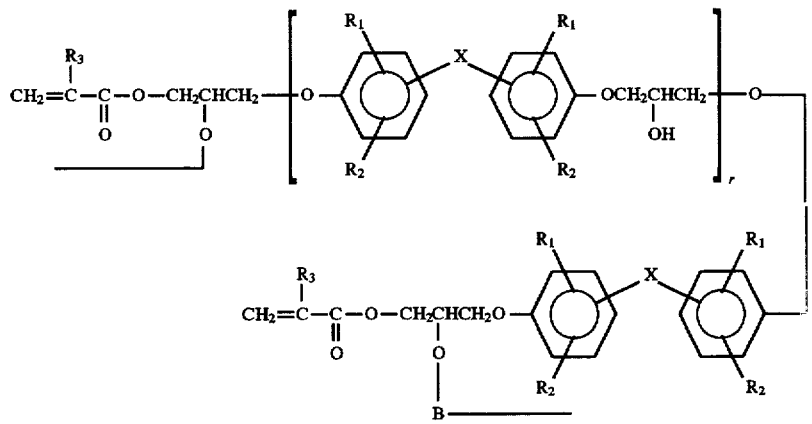

Acid anhydrides capable of introducing the group Y are, for example, maleic anhydride, succinic anhydride, itaconic anhydride, phthalic anhydride, tetrahydrophthalic anhydride, hexahydrophthalic anhydride, methylendomethylenetetrahydrophthalic anhydride, chlorendic anhydride, methyltetrahydrophthalic anhydride and trimellitic anhydride. They may be used singly or as a mixture of two or more. In the compounds of the general formula (4), those with either t=0 or t=1 or those containing an arbitrary mixture of t=0 and t=1 may be used. Acid dianhydrides capable of introducing the group Z are aromatic polycarboxylic acid anhydrides such as pyromellitic anhydride, benzophenonetetracarboxylic acid dianhydride, biphenyltetracarboxylic acid dianhydride, and diphenyl ether tetracarboxylic acid dianhydride.

As for the molecular weight of the products mainly consisting of the compounds represented by the general formulas (4) and (5), those products with a molecular weight of 0.1 dl/g or more, preferably 0.15 dl/g or more, in terms of inherent viscosity ($\eta_{inh}$) as measured on a solution of 0.5 g of the products in 100 ml of N-methylpyrrolidone at 30° C. form tack-free films after drying.

The ratio of acid anhydride to acid dianhydride here can be chosen at will, but it is preferable from the standpoint of alkali developability to choose a mol ratio m/n of 1/99 to 90/10 where m stands for acid anhydride and n for acid dianhydride.

The photosensitive resin compositions of low curing shrinkage of this invention are suitable for the formation of fine patterns by exposure and alkali development as described above. No restriction is imposed on the ratio of acid anhydride to acid dianhydride in the cases where the compositions are used for patterning by the conventional screen printing without need of fine patterns or where they are used as molding materials and adhesives without involving patterning.

The reaction of epoxy (meth)acrylates with polybasic acids or their anhydrides for the preparation of the aforementioned compounds is carried out in the following manner.

For example, bisphenolfluorene-based epoxy resins represented by the following general formula (6) obtained by the reaction of 9,9-bis(4-hydroxyphenyl)fluorene with epichlorohydrin is subjected to the reaction with (meth)acrylic acid represented by the following general formula (7) to yield bisphenolfluorene-based epoxy acrylates represented by the following general formula (8), which are heated with the aforementioned acid anhydrides in a cellosolve solvent such as ethyl cellosolve acetate and butyl cellosolve acetate. The reaction temperature is desirably set so that ½ mol of the acid anhydride reacts quantitatively with 1 mol of the hydroxyl group in the epoxy acrylates or it is 90° to 130° C., preferably 95° to 125° C. This reaction is carried out similarly in the preparation of the compounds with the structural units represented by the general formulas (4) and (5).

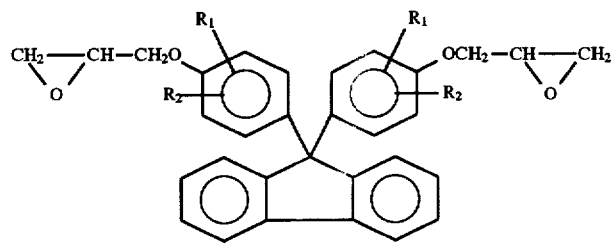

(6)

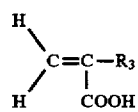

(7)

-continued

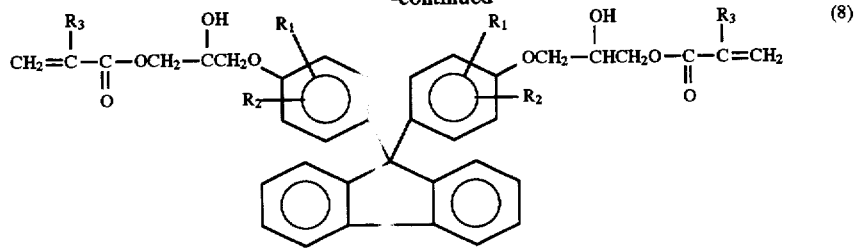

(8)

The aforementioned general formulas (6) and (8) are shown in a simplified form like the general formulas (4) and (5). The formulas of the oligomers corresponding to the cases where r=1 to 10 can also be shown as before.

The resin compositions of low curing shrinkage of this invention contain the aforementioned (meth)acrylates and, in addition, photopolymerization initiators and sensitizers or radical polymerization initiators to effect photo-curing or thermal curing.

The component B for photo-curing of the component A in this invention, that is, photopolymerization initiators and sensitizers, is used not only for the aforementioned component h but also for photopolymerizable unsaturated compounds such as (meth)acrylic monomers and oligomers which are added as needed.

Photopolymerization initiators and sensitizers useful as the component B are, for example, acetophenones such as acetophenone, 2,2-diethoxyacetophenone, p-dimethylacetophenone, p-dimethylaminopropiophenone, dichloroacetophenone, trichloroacetophenone and p-tert-butylacetophenone, benzophenones such as benzophenone, 2-chlorobenzophenone and p,p'-bisdimethylaminobenzophenone benzil, benzoin, benzoin ethers such as benzoin methyl ether, benzoin isopropyl ether and benzoin isobutyl ethers, benzil dimethyl ketal, sulfur compounds such as thioxanthone, 2-chlorothioxanthone, 2,4-diethylthioxanthone, 2-methylthioxanthone and 2-isopropylthioxanthone, anthraquinone such as 2-ethylanthraquinone, octamethylanthraquinone, 1,2-benzanthraquinone and 2,3-diphenylanthraquinone, azobisisobutyronitrile, organic peroxides such as benzoyl peroxide and cumene peroxide and thiols such as 2-mercaptobenzimidazole, 2-mercaptobenzoxazole and 2-mercaptobenzothiazole.

The aforementioned compounds may be used singly or as a mixture of two or more. Moreover, they can be used in admixture with those compounds which do not act as photopolymerization initiator by themselves but help to enhance the ability of photopolymerization initiators when used in combination with the aforementioned compounds. An example of such compounds is a tertiary amine: triethanolamine is effective when used in combination with benzophenone. An adequate proportion of the component B such as described above is 0. 1 to 30 parts by weight per 100 parts by weight of the component A. With less than 0.1 part by weight of the component B, the rate of photopolymerization drops with the resultant drop in sensitivity. On the other hand, the presence of more than 30 parts by weight of the component B makes it difficult for light to reach the inside and the portions left uncured deteriorate the properties, for example, loss in adhesion between substrate and resin.

The heat-curable resin compositions of low curing shrinkage of this invention contain the aforementioned (meth) acrylate compounds and radical polymerization initiators to effect thermal curing. Thus, the compositions cure by heating.

The component B or radical polymerization initiators used here for curing the component A generates radicals by heating and is used as polymerization initiator not only for the component h but also for heat-polymerizable (meth) acrylic monomers and oligomers which are added as needed.

The radical polymerization initiators used as the component B can be the hitherto known peroxides and azobis compounds. Examples of peroxide-based initiators are the following: ketone peroxides such as methyl ethyl ketone peroxide, methyl isobutyl ketone peroxide, cyclohexanone peroxide, methyl cyclohexanone peroxide and acetylacetone peroxide; diacyl peroxides such as isobutyryl peroxide, m-chlorobenzoyl peroxide, 2,4-dichlorobenzoyl peroxide, o-methylbenzoyl peroxide and bis-3,5,5-trimethylhexanoyl peroxide; hydroperoxides such as 2,4,4-trimethylpentyl-2-hydroperoxide, diisopropylbenzene hydroperoxide and t-butyl hydroperoxide; dialkyl peroxides such as dicumyl peroxide, 2,5-dimethyl-2,5-di(t-butylperoxy)hexane, 1,3-bis (t-butylperoxyisopropyl)benzene and t-butyl cumyl peroxide; peroxyketals such as 1,1-di-t-butylperoxy-3,3,5-trimethylcyclohexane, 2,2-di-(t-butylperoxy)butane and 4,4-di-t-butylperoxyvaleric acid n-butyl ester; alkyl peroxyesters such as 2,4,4-trimethylpentyl peroxyphenoxyacetate, α-cumyl peroxyneodecanoate and t-butyl peroxytrimethyladipate; percarbonates such as di-3-methoxybutyl peroxydicarbonate, di-2-ethylhexyl peroxydicarbonate, bis (4-t-butylcyclohexyl) peroxydicarbonate and diisopropyl peroxydicarbonate; acetylcyclohexylsulphonyl peroxydicarbonate and t-butylperoxy allyl carbonate.

Examples of azobis compound-based initiators are 1,1'-azobiscyclohexane-1-carbonitrile, 2,2'-azobis-(2,4-dimethylvaleronitrile), 2,2'-azobis-(4-methoxy-2,-dimethylvaleronitrile), 2,2'-azobis-(methylisobutyrate), α,α'-azobis(isobutyronitrile) and 4,4'-azobis-(4-cyanovaleric acid).

The aforementioned radical polymerization initiators may be used singly or as a mixture of two or more and 0.1 to 10 parts by weight of the component C is added to 100 parts by weight of the component A. Addition of less than 0.1 part by weight of the component C to 100 parts by weight of the component A lowers the rate of polymerization while addition in excess of 10 parts by weight lowerd the molecular weight of the cured product, which results in insufficient heat resistance and poor adhesion of resin to substrate.

In the photosensitive or heat-curable resin compositions of low curing shrinkage of this invention, 5 to 100 parts by weight of the component C, that is, compounds represented by the aforementioned general formula (3) containing two or more ortho spiroester groups in the molecule, to 100 parts by weight of the component A in order to improve the moisture resistance, adhesive properties and stability of electrical insulation of the products after photo-curing and alkali development or heat curing of the respective resin compositions.

In the resin compositions of low curing shrinkage of this invention, the incorporation of the component C reduces curing shrinkage after heating and produces a variety of beneficial effects such as prevention of decrease in film thickness, improvement of dimensional stability of patterns obtained by printing and improvement in adhesion to transparent electrodes such as glass and ITO (indium tin oxide) when used as coating materials and improvement of dimensional accuracy and adhesive strength when used as adhesives. As molding materials, the compositions cure with improved dimensional stability, reduced residual strain and optical deformation and excellent moisture resistance, transparency, surface hardness, smoothness, heat resistance and chemical resistance. The curing is effected, for example, at 80° to 220° C. for 10 to 120 minutes.

The ortho spiroesters constituting the photosensitive or heat-curable resin compositions of this invention are, for example, those prepared by treating lactones such as γ-butyrolactone, δ-valerolactone and ε-caprolactone with epoxy compounds of the general formula A(OG)$_n$ (wherein A is an organic group of n valence, G is glycidyl group and n is an integer of 2 or more, preferably 2).

Epoxy compounds useful for this reaction are, for example, aromatic polyfunctional epoxy resins containing two or more glycidyl ether groups on the average in the molecule prepared by the reaction of epichlorohydrin with the following phenolic compounds: bis(4-hydroxyphenyl) ketone, bis(4-hydroxy-3,5-dimethylphenyl) ketone, bis(4-hydroxy-3,5-dichlorophenyl)ketone, bis(4-hydroxyphenyl) sulfone, bis(4-hydroxy-3,5-dimethylphenyl)sulfone, bis(4-hydroxy-3,5-dichlorophenyl)sulfone, bis(4-hydroxyphenyl) hexafluoropropane, bis(4-hydroxy-3,5-dimethylphenyl) hexafluoropropane, bis(4-hydroxy-3,5-dichlorophenyl) hexafluoropropane, bis(4-hydroxyphenyl)dimethylsilane, bis(4-hydroxy-3,5-dimethylphenyl)dimethylsilane, bis(4-hydroxy-3,5-dichlorophenyl)dimethylsilane, bis(4-hydroxyphenyl)methane, bis(4-hydroxy-3,5-dichlorophenyl)methane, bis(4-hydroxy-3,5-dibromophenyl)methane, 2,2-bis(4-hydroxyphenyl) propane, 2,2-bis(4-hydroxy-3,5-dimethylphenyl)propane, 2,-bis(4-hydroxy-3,5-dichlorophenyl)propane, 2,2-bis(4-hydroxy-3-methylphenyl)propane, 2,2-bis(4-hydroxy-3-chlorophenyl)propane, bis(4-hydroxyphenyl)ether, bis(4-hydroxy-3,5-dimethylphenyl)ether, and bis(4-hydroxy-3,5-dichlorophenyl)ether; phenols containing the skeleton of

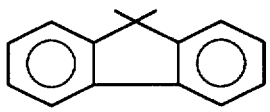

such as 9,9-bis(4-hydroxyphenyl)fluorene, 9,9-bis(4-hydroxy-3-methylphenyl)fluorene, 9,9-bis(4-hydroxy-3-chlorophenyl)fluorene, 9,9-bis(4-hydroxy-3-bromophenyl) fluorene, 9,9-bis(4-hydroxy-3-fluorophenyl)fluorene, 9,9-bis(4-hydroxy-3-methoxyphenyl)fluorene, 9,9-bis(4-hydroxy-3,5-dimethylphenyl)fluorene, 9,9-bis(4-hydroxy-3,5-dichlorophenyl)fluorene, and 9,9-bis(4-hydroxy-3,5-dibromophenyl)fluorene; 4,4'-biphenol, 3,3'-biphenol, resorcinol, phenol novolaks, cresol novolaks, naphthol novolaks and condensation products of phenol or naphthol and 1,4-benzenedimethanol. The following epoxy compounds are also known: polycarboxylic acid glycidyl esters obtained by the reaction of carboxyl group-containing compounds such as adipic acid, sebacic acid, phthalic acid and hexahydrophthalic acid with epichlorohydrin; aliphatic polyfunctional epoxy resins, for example, EHPE3150 manufactured by Daicel Chemical Industries, Ltd.; polyol polyglycidyl ethers; alicyclic epoxy resins containing 2 or more internal epoxy groups on the average in the molecule, for example, Chissonox 201, 221, 289, 206, 207 and 1221 manufactured by Chisso Corporation and Celloxide 2021P manufactured by Daicel Chemical Industries, Ltd.; epoxidized olefins and polybutadiene; and isocyanuric acid-derived epoxy resins and nitrogen-containing heterocycle-based epoxy resins derived from derivatives of hydantoin or imidazoline.

The proportion of the aforementioned ortho spiroesters is preferably 5 to 100 parts by weight per 100 parts by weight of the component A. Addition of less than 5 parts by weight of the component B to 100 parts by weight of the component A does not produce the effect characteristic of ortho spiroesters to any appreciable degree. On the other hand, addition in excess of 100 parts by weight may not display sufficient heat resistance in some of ortho spiroesters and also adversely affects the alkali developability after photocure in the case of photosensitive resin compositions of low curing shrinkage.

In the event that ortho spiroesters are chosen for the purpose of improving the heat resistance, candidates with two ortho spiroester groups in the molecule are compounds containing bulky aromatic rings, for example, fluorene rings, such as represented by the following general formula (1)

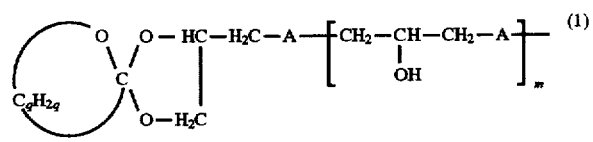

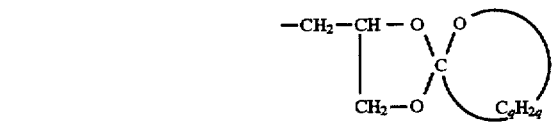

[wherein A is

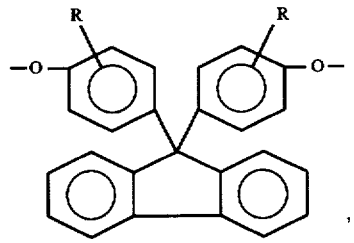

,

R$_1$ and R$_2$ are as defined in the general formulas (4) and (5), m is 0 or an integer from 1 to 10 and q is as defined in the general formula (1)]. They help to exhibit good heat resistance without an appreciable increase in the crosslinking density.

Examples of such compounds are ortho spiroesters obtained by the reaction of lactones with epoxy compounds derived from 9,9-bis(4-hydroxyphenyl)fluorene, 9,9-bis(4-hydroxy-3-methylphenyl)fluorene, 9,9-bis(4-hydroxy-3-chlorophenyl)fluorene, 9,9-bis(4-hydroxy-3-bromophenyl) fluorene, 9,9-bis(4-hydroxy-3-fluorophenyl)fluorene, 9,9-bis(4-hydroxy-3-methoxyphenyl)fluorene, 9,9-bis(4-hydroxy-3,5-dimethylphenyl)fluorene, 9,9-bis(4-hydroxy-3,5-dichlorophenyl)fluorene, and 9,9-bis(4-hydroxy-3,5-dibromophenyl)fluorene. These compounds are found to be effective in small amounts for decreasing curing shrinkage.

In order to produce the same effect, it is desirable to add aromatic compounds containing three or more ortho spiroesters in the molecule. Concrete examples of such compounds are polyfunctional ortho spiroesters derived from epoxy resins which are obtained by the reaction of epichlorohydrin with phenolic compounds such as phenol novolaks, cresol novolaks, naphthol novolaks and condensation products of phenol or naphthol and 1,4- benzenedimethanol. They are also found to be effective in small amounts for decreasing curing shrinkage.

The component A can be combined effectively with the component C at an arbitrary ratio as long as such combination does not affect the miscibility of the two in the course of the preparation of resin compositions of low curing shrinkage and the ratio is chosen according to end uses.

It is possible to add, besides the aforementioned component A, photopolymerizable or heat-polymerizable monomers and oligomers containing ethylchic unsaturation to resin compositions of low curing shrinkage of this invention within a specified range. Such monomers include the following (meth)acrylate esters; 2-hydroxyethyl (meth)acrylate, 2-hydroxypropyl (meth)acrylate, 2-ethylhexyl (meth)acrylate, ethylene glycol di(meth)acrylate, diethylene glycol di(meth)acrylate, triethylene glycol di(meth)acrylate, tetraethylene glycol di(meth)acrylate, tetramethylene glycol di(meth)acrylate, trimethylolpropane tri(meth)acrylate, trimethylolethane tri(meth)acrylate, pentaerythritol di(meth)acrylate, pentaerythritol tri(meth)acrylate, pentaerythritol tetra(meth)acrylate, dipentaerythritol tetra(meth)acrylate, dipentaerythritol hexa(meth)acrylate and glycerol (meth)acrylate. They can be used singly or as a mixture of two or more.

It is necessary to keep the addition of these compounds in a range within which the resin compositions of low curing shrinkage of this invention and their cured products suffer no deterioration of their properties and normally 50 parts by weight or less is used per 100 parts by weight of the component A. Addition in excess of 50 parts by weight causes a problem in tack after precure.

Moreover, some epoxy resins which have remained unchanged after the preparation of the aforementioned component C may be present in the resin compositions of low curing shrinkage of this invention or certain end uses permit addition of epoxy resins to the compositions within a range which does not deteriorate the properties of cured products. In such a case, the presence of less than 50 parts by weight, preferably less than 40 parts by weight, of epoxy resins per 100 parts by weight of the component C is deistable in order for the ortho spiroesters (component C) to exercise fully their function of lowering curing shrinkage.

It is also possible to use, as needed, such additives as curing accelerators, thermal polymerization inhibitors, plasticizers, fillers, solvents, leveling agents and anti-foaming agents in formulating the aforementioned resin compositions of low curing shrinkage.

Curing accelerators for ortho spiroester groups include amines, imidazoles, 1,8-diazabicyclo(5,4,0)undecene-7 and its salt, boron trifluoride-amine complexes, organic sulfonium salts which generate Lewis acids by heat, carboxylic acids, phenols, quaternary ammonium salts and methylol group-containing compounds. Films formed by resin compositions containing a small amount of these curing accelerators cure by heating with improvements in such properties as resistance to heat, solvents, acids and plating, adhesive properties, electrical properties and hardness.

The aforementioned thermal polymerization inhibitors include hydroquinone, hydroquinone monomethyl ether, pyrogallol, tert-butylcatechol and phenothiazine. Plasticizers include dibutyl phthalate, dioctyl phthalate and tricresyl phosphate. Fillers include glass fibers, silica, mica and alumina and they may be added to fig the end use.

In the event that the resin compositions of low curing shrinkage of this invention are used as coatings or adhesives, they may be diluted with solvents to adjust the viscosity. The solvents useful for this purpose are, for example, ketones such as methyl ethyl ketone and methyl isobutyl ketone, cellosolves such as methyl cellosolve, ethyl cellosolve, butyl cellosolve and cellosolve acetate and lactones such as γ-butyrolactone.

Anti-foaming agents and leveling agents include silicones, fluorine-containing compounds and acrylic compounds.

The photosensitive or heat-curable resin compositions of low curing shrinkage of this invention are used as molding materials, coatings for electrically insulating films, adhesives, printing inks and coatings. They undergo low curing shrinkage after heating by the action of the component C and produce a variety of beneficial effects such as prevention of decrease in film thickness, improvement of dimensional stability of patterns obtained by printing and improvement in adhesion to transparent electrodes such as glass and ITO (indium tin oxide) when used as coating materials and improvement in dimensional accuracy and adhesive strength when used as adhesives. As molding materials, the compositions cure with improved dimensional stability, reduced residual strain and optical deformation and excellent moisture resistance, transparency, surface hardness, smoothness, heat resistance and chemical resistance.

When the photosensitive resin compositions of low curing shrinkage are used as coatings, they are dissolved in a solvent, applied to the surface of a substrate, dried by removing the solvent by precure, covered with a nagative film, exposed to active light to cure the exposed portion, and treated with a weakly alkaline aqueous solution to dissolve off the unexposed portions to form patterns.

Coating of the substrate with a solution of the resin compositions can be carried out by any one of known processes such as dippping and spraying and also with the aid of a roll coater, a Landcoarter and a spinner. The solution is thus applied to a specified thickness and stripped of the solvent to form a film.

A substrate to be used in coating is, for example, glass or a transparent film [for example, polycarbonate, poly (ethylene terephthalate) and polyetherpolysulfone] on which a transparent electrode such as ITO or gold, and metal such as aluminum or steel, respectively, are metallized and patterned.

Light suitable for curing the photosensitive resin compositions of low curing shrinkage of this invention is the one generated by ultrahigh-pressure mercury lamps, high-pressure mercury lamps or metal halide lamps.

A developing solution suitable for the alkali development of the photosensitive resin compositions of low curing shrinkage of this invention is, for example, an aqueous solution of carbonates of alkali metal or alkaline earth metals or hydroxides of alkali metals. In particular, development with a weakly alkaline solution of alkali metal carbonate such as sodium carbonate, potassium carbonate and lithium carbonate at 10° to 50° C., preferably at 20° to 40° C., with the use of commercially available developing equipment and ultrasonic cleaners allows formation of fine images with precision.

After development, heat treatment is conducted at 80° to 220° C. for 10 to 120 minutes. The component C, that is, the ortho spiroesters, undergoes small shrinkage during curing and contributes to the dimensional stability of resist patterns and improves further the moisture resistance, chemical resistance, adhesive properties and electrical insulation.

The photosensitive resin compositions of low curing shrinkage of this invention is suited for the formation of fine patterns by exposure to light and development by alkali as described above. Likewise, the compositions provide cured products with excellent adhesive properties, transparency, surface hardness, smoothness, moisture resistance, electrical insulation, heat resistance and chemical resistance when applied to patterning by the conventional screen printing.

When the heat-curable resin compositions of low curing shrinkage of this invention are used as coatings, the compositions are dissolved in a solvent, applied to the surface of a substrate, dried to remove the solvent by precure at 50° to 80° C., and postcured at 80° to 220° C. to form a cured film. It is also possible to use the resin compositions for patterning by screen printing. In the latter case, a solution of the compositions is applied to a substrate, dried for removal of the solvent and cured in the same manner as above for the photosensitive resin compositions.

The photosensitive or heat-curable resin compositions of low curing shrinkage of this invention are used advantageously as coatings and are particularly useful as compositions for protection of color filters to be used in liquid-crystal displays or photographing devices, for inks for color filters and for color filters composed of such resin compositions and inks. Furthermore, the compositions are useful as spacers constituting electrically insulating separators in touch panels for information input installed in the upper part of a liquid-crystal display.

For example, when the resin compositions of this invention are used as protective films for color filers, the compositions are formulated mainly from the components A, B and C.

In the case of inks for color filters, the compositions are formulated from the components A, B and C and additionally pigments as component D for coloring the films.

The pigments to be used here include organic and inorganic pigments. Examples of organic pigments are azo lakes, insoluble azo pigments, phthalocyanines, quinacridones, dioxazines, isoindolinones, perinone pigments, anthraquinone pigments, perylene pigments and their mixtures. Examples of inorganic pigments are milori blue, iron oxide, cobalt-based pigments, manganese-based compounds, ultramarine blue, Prussian blue, cobalt blue, cerulean blue, viridian, emerald green, cobalt green and their mixtures. In order to color films while maintaining their transparency, the pigments in practical use are preferably dispersed to a particle size of 0.4 μm which is the lower limit of visible light or less, preferably to an average particle size of 0.2 to 0.3 μm. Addition of less than 10 parts by weight of pigments per 100 parts by weight of the sum of the components A and C does not give the desired spectral properties while addition in excess of 200 parts by weight lowers the adhesive strength of films.

In addition to the aforementioned color filters for color liquid-crystal displays and their protective films, the photosensitive or heat-curable resin compositions of this invention are used as multicolor inks for color liquid-crystal displays, color facsimile and image sensors and protective films.

When the photosensitive or heat-curable resin compositions of this invention are used as spacers for touch panels, the substrates to which the compositions are applied are glass or transparent films [for example, polycarbonate, poly (ethylene terephthalate) and polyetherpolysulfone] metallized with transparent electrodes such as ITO, gold or the like or with their patterns although they may vary with the shape touch panels in use and with the environment. Whatever the substrate may be, the compositions equally provide spacers for touch panels with excellent adhesion, transparency, surface hardness, smoothness, moisture resistance, electrical insulation, heat resistance and chemical resistance.

PREFERRED EMBODIMENTS OF THE INVENTION

This invention will be described in detail below with reference to the accompanying examples and comparative examples.

EXAMPLE 1

Into a four-necked flask fitted with a stirrer, a condenser, a thermometer and a dropping funnel were introduced 50 g of methylene chloride and 17.2 g (0. mol) of γ-butyrolactone and to the resulting solution was added 0.80 ml (0.0062 mol) of boron trifluoride-diethyl ether complex while cooling the solution at 10° C.

Thereafter, a mixture of 26.0 g (0.1 equivalent) of epoxy resins of the aforementioned general formula (2) (R=H; epoxy equivalent, 260) and 200 g of methylene chloride was added in drops with stirring over a period of 5 hours to effect the reaction while keeping the temperature at 5° to 10° C. After completion of the dropwise addition, the reaction mixture was stirred for additional 3 hours at a constant temperature and 0.72 g (0.0072 mol) of triethylamine (reaction terminator) was added.

The reaction mixture was washed with 500 ml of a 6% aqueous solution of sodium hydroxide twice and then washed with 500 ml of distilled water twice to remove the excess γ-butyrolactone. The organic layer was separated, dried with magnesium sulfate and stripped of the solvent to yield ortho spiroesters [R=H, m=1.13 (average) and q=4 in the general formula (1)].

Figure 1:
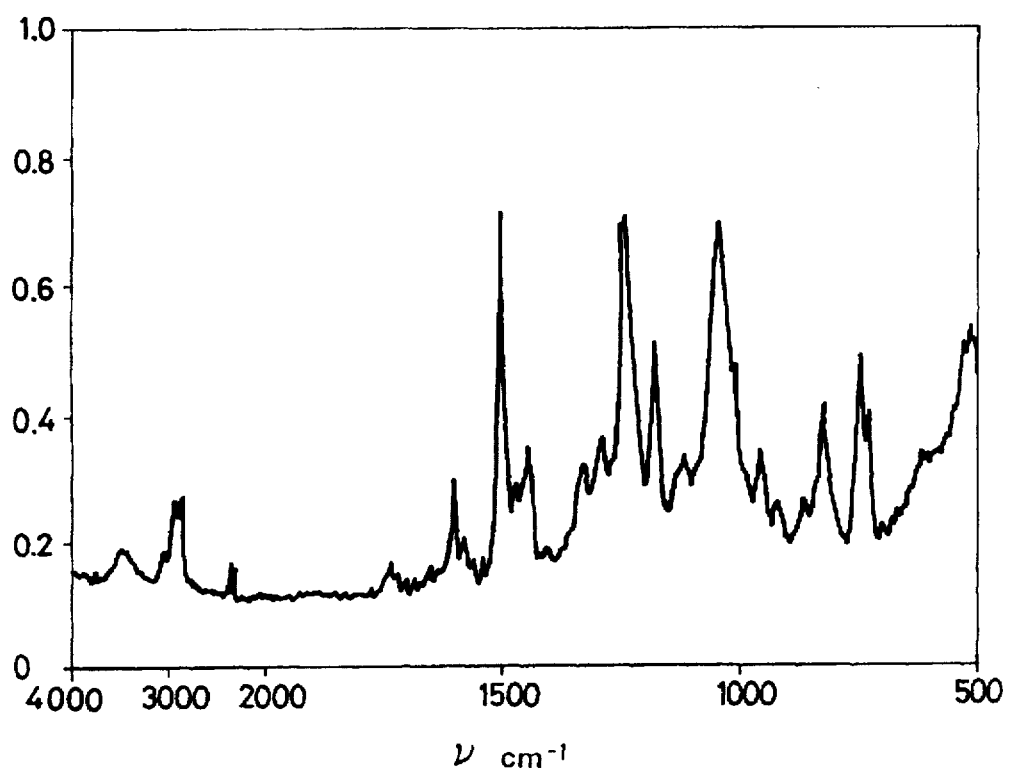
FIG. 1 is an infrared absorption spectrum of the ortho spiroesters obtained in Example 1.
Figure 2:
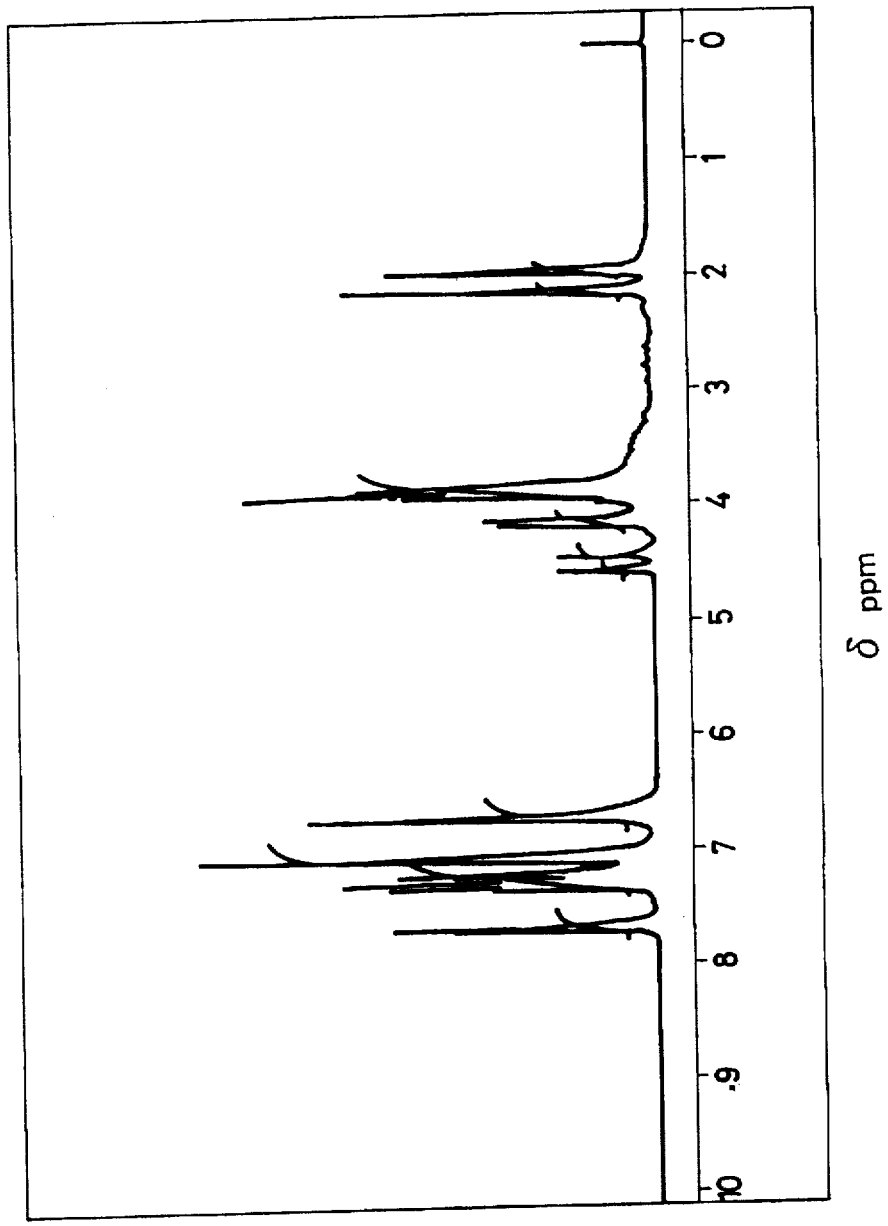
FIG. 2 is a nuclear magnetic resonance spectrum of the ortho spiroesters obtained in Example 1.

The yield of the products was 30.4 g (88%) and their infrared absorption spectrum and nuclear magnetic resonance spectrum ($CDCl_3$) are respectively shown in FIGS. 1 and 2.

EXAMPLE 2

Into a four-necked flask fitted with a stirrer, a condenser, a thermometer and a dropping funnel were introduced 50 g of methylene chloride and 22.9 g (0. mol) of ε-caprolactone and to the resulting solution was added 0.80 ml (0.0062 mol) of boron trifluoride-diethyl ether complex while cooling the solution at 10° C.

Thereafter, a mixture of 26.0 g (0.1 equivalent) of epoxy resins of the aforementioned general formula (2) (R=H; epoxy equivalent, 260) and 200 g of methylene chloride was added in drops with stirring over a period of 5 hours to effect the reaction while keeping the temperature at 5° to 10° C. After completion of the dropwise addition, the reaction mixture was stirred for additional 3 hours at a constant temperature and 0.72 g (0.0072 mol) of triethylamine (reaction terminator) was added.

The reaction mixture was washed with 500 ml of a 6% aqueous solution of sodium hydroxide twice and then washed with 500 ml of distilled water twice to remove the excess ε-caprolactone. The organic layer was separated, dried with magnesium sulfate and stripped of the solvent to yield ortho spiroesters.

Figure 3:
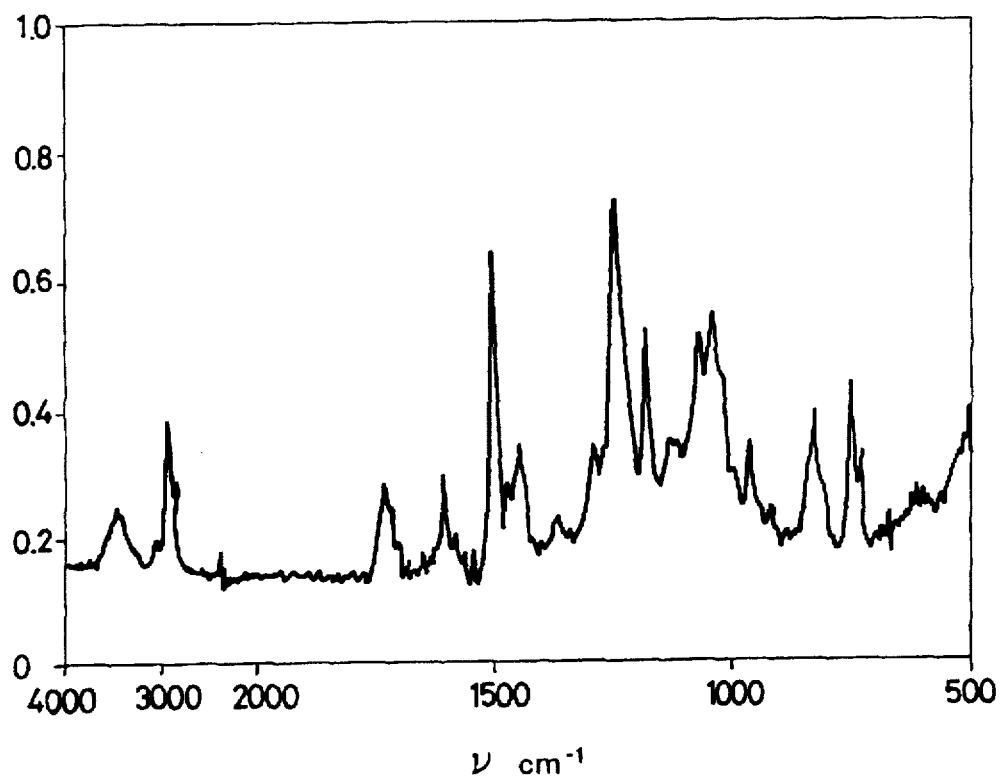
FIG. 3 is an infrared absorption spectrum of the ortho spiroesters obtained in Example 2.
Figure 4:
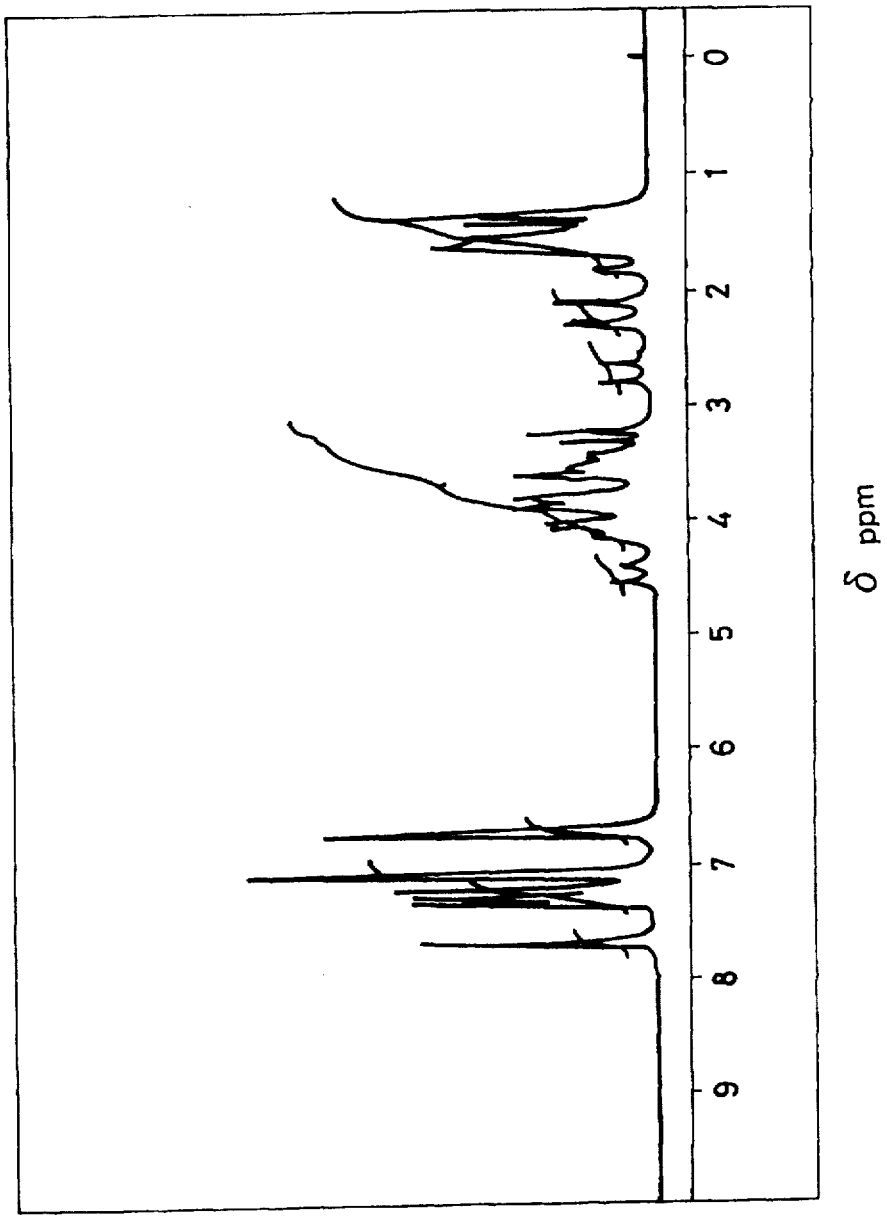
FIG. 4 is a nuclear magnetic resonance spectrum of the ortho spiroesters obtained in Example 2.

The yield of the products was 29.5 g (79%) and their infrared absorption spectrum and nuclear magnetic resonance spectrum ($CDCl_3$) are respectively shown in FIGS. 3 and 4.

EXAMPLE 3

A resin composition was formulated from the ortho spiroesters obtained in Example 1,4-methylcyclohexane-1, 2-dicarboxylic acid anhydride (molecular weight 168) and 2MA-OK (imidazole-based curing accelerator manufactured by Shikoku Chemicals Corporation) at the weight ratio shown in Table 1.

The resin composition was tested for its specific gravity at 25° C. as prepared and also as cured after heating at 120° C. for 2 hours and then at 150° C. for 15 hours. The shrinkage in volume was calculated from the difference in specific gravity before and after curing. The glass transition temperature was determined by TMA (thermomechanical analysis). The results are shown in Table 1.

Comparative Example 1

A resin composition was formulated from bisphenol A-based ortho spiroesters ( γ-butyrolactone adducts), 4-methylcyclohexane-1,2-dicarboxylic acid anhydride and 2MA-OK at the weight ratio shown in Table 1.

The resin composition was tested for its specific gravity at 25° C. as prepared and also as cured after heating at 120° C. for 2 hours and then at 150° C. for 15 hours. The shrinkage in volume was calculated from the difference in specific gravity before and after curing. The glass transition temperature was determined by TMA. The results are shown in Table 1.

Comparative Example 2

A resin composition was formulated from bisphenol A-based ortho spiroesters (γ-butyrolactone adducts), Epikote 828, 4-methylcyclohexane-1,2-dicarboxylic acid anhydride and 2MA-OK at the weight ratio shown in Table 1.

The resin composition was tested for its specific gravity at 25° C. as prepared and also as cured after heating at 120° C. for 2 hours and then at 150° C. for 15 hours. The shrinkage in volume was calculated from the difference in specific gravity before and after curing. The glass transition temperature was determined by TMA. The results are shown in Table 1.

TABLE 1

| | | Component of resin composition (wt part) | | | | | | | | | Volume shrinkage (%) | Glass transition temperature (°C.) |
|---|---|---|---|---|---|---|---|---|---|---|---|---|
| | | A | B | C | D | E | F | G | H | I | | |
| Example | 3 | 100 | — | — | — | — | 39 | 3 | — | — | −3.6*[1] | 121 |
| | 4 | 30 | — | — | 70 | — | 84 | 3 | — | — | 2.01 | 171 |
| | 5 | 30 | — | — | 70 | — | 84 | — | — | 3 | 1.87 | 175 |
| | 6 | 30 | — | — | — | 70 | 61 | 3 | — | — | 0.87 | 142 |
| | 7 | 50 | — | — | 50 | — | 71 | 3 | — | — | 0.32 | 144 |
| | 8 | 50 | — | — | — | 50 | 55 | 3 | — | — | 0.02 | 124 |
| | 9 | — | 20 | — | 80 | — | 89 | 3 | — | — | 1.91 | 165 |
| | 10 | — | 30 | — | 70 | — | 83 | 3 | — | — | 1.71 | 150 |
| | 11 | 30 | — | — | — | 70 | — | — | 30 | — | 1.21 | 154 |
| Comparative example | 1 | — | — | 100 | — | — | 42 | 3 | — | — | −0.4*[1] | 64 |
| | 2 | — | — | 30 | — | 70 | 64 | 3 | — | — | 2.13 | 91 |

(Notes)
Component
A: Ortho spiroesters of Example 1
B: Ortho spiroesters of Example 2
C: Bisphenol A-based ortho spiroesters (γ-butyrolactone adducts)
D: Celloxide 2021P
E: Epikote 828
F: 4-Methylcyclohexane-1,2-dicarboxylic acid
G: 2MA-OK
H: Epicure 170
I: Boron trifluoride-monoethylamine complex
*[1]: Expansion EXAMPLES 4 to 11

Eight resin compositions, one for each of Examples 4 to 11, were formulated from the ortho spiroesters obtained in Example 1 or 2, Epikote 828 (bisphenol A-based epoxy resin with epoxy equivalent 189 manufactured by Yuka Shell Epoxy K.K.), Celloxide 2021P (alicyclic epoxy resin with epoxy equivalent 131 manufactured by Daicel Chemical Industries, Ltd.), 4-methylcyclohexane-1,2-dicarboxylic acid anhydride (molecular weight 168), Epicure 170 (manufactured by Yuka Shell Epoxy K.K.), 2MA-OK (imidazole-based curing accelerator) and boron trifluoride-monoethylamine complex at the weight ratio shown in Table 1.

Each resin composition was tested for its specific gravity at 25° C. as prepared and also as cured after heating at 120° C. for 2 hours and then at 150° C. for 15 hours. The shrinkage in volume was calculated from the difference in specific gravity before and after curing. The glass transition temperature was determined by TMA. The results are shown in Table 1.

The photosensitive or heat-curable resin compositions of low curing shrinkage of this invention will be described in detail with reference to the accompanying synthetic examples, examples and comparative examples.

The synthesis of the component A of this invention or photo- or heat-polymerizable compounds is described in Synthetic Examples 1 to 14.

Synthetic Example 1

Into a 500-ml four-necked flask were introduced 231 g of bisphenolfluorene-based epoxy resins (epoxy equivalent 231), 450 mg of triethylbenzylammonium chloride, 100 mg of 2,6-diisobutylphenol and 72.0 g of acrylic acid and the mixture was heated at 90° to 100° C. with air blown in at a rate of 25 ml/min. The resulting solution which was turbid was gradually heated up as it was and heated at 120° C. to effect complete dissolution. The solution gradually became transparent and viscous and the heating was continued with stirring until the acid value, determined at intervals, became less than 2.0 mgKOH/g. It required 8 hours for the acid value to reach the target of 0.8. The solution was then cooled down to room temperature to yield a colorless transparent solid.

A solution prepared by adding 2 kg of cellosolve acetate to 303 g of the bisphenolfluorene-based epoxy acrylates obtained above was mixed with 38 g of 1,2,3,6-tetrahydrophthalic anhydride, 80.5 g of benzophenonetetra-carboxylic acid dianhydride and 1 g of tetraethylammonium bromide and the mixture was gradually heated up and kept at 110° to 115° C. for 2 hours to yield Compound 1 (m/n =50/50). The reaction with the acid anhydrides was confirmed by infrared spectrometry by the disappearance of the peak at 1780 cm$^{-1}$. The compound showed an inherent viscosity of 0.3 dl/g ($\eta_{inh}$=0.3).

Synthetic Example 2

A solution of 303 g of the bisphenolfluorene-based epoxy acrylates prepared in Synthetic Example 1 in 2 kg of cellosolve acetate was mixed with 121.6 g of 1,2,3,6-tetrahydrophthalic anhydride, 64.6 g of benzophenonetetra-carboxylic acid dianhydride and 1 g of tetraethylammonium bromide and the mixture was gradually heated up and kept at 110° to 115° C. for 2 hours to yield Compound 2 (m/n=80/20). The reaction with the acid anhydrides was confirmed by infrared spectrometry as in Synthetic Example 1. The compound showed an inherent viscosity of 0.2 dl/g ($\eta_{inh}$=0.2).

Synthetic Example 3

A solution of 303 g of the bisphenolfluorene-based epoxy acrylates prepared in Synthetic Example 1 in 2 kg of cellosolve acetate was mixed with 3.8 g of 1,2,3,6-tetrahydrophthalic anhydride, 153.8 g of benzophenonetetra carboxylic acid dianhydride and 1 g of tetraethylammonium bromide and the mixture was gradually heated up and kept at 110° to 115° C. for 2 hours to yield Compound 3 (m/n=0.5/99.5). The reaction with the acid anhydrides was confirmed by infrared spectrometry. The compound showed an inherent viscosity of 0.3 dl/g ($\eta_{inh}$=0.3).

Synthetic Example 4

A solution of 303 g of the bisphenolfluorene-based epoxy acrylates prepared in Synthetic Example 1 in 2 kg of cellosolve acetate was mixed with 144.4 g of 1,2,3,6-tetrahydrophthalic anhydride, 16.1 g of benzophenonetetra-carboxylic acid dianhydride and 1 g of tetraethylammonium bromide and the mixture was gradually heated up and kept at 110° to 115° C. for 2 hours to yield Compound 4 (m/n=95/5). The reaction with the acid anhydrides was confirmed by infrared spectrometry. The compound showed an inherent viscosity of 0.2 dl/g ($\eta_{inh}$=0.2).

Synthetic Example 5

The epoxy acrylates prepared as in Synthetic Example 1 except using 153 g of biphenyl-based epoxy resins (epoxy equivalent 153) in place of the bisphenolfluorene-based epoxy resins were allowed to react with the acid anhydrides as in Synthetic Example 1 to yield Compound 5 (m/n=50/50). The reaction with the acid anhydrides was confirmed by infrared spectrometry. The compound showed an inherent viscosity of 0.2 dl/g ($\eta_{inh}$=0.2).

Synthetic Example 6

The epoxy acrylates prepared as in Synthetic Example 1 except using 163 g of benzophenone-based epoxy resins (epoxy equivalent 163) in place of the bisphenolfluorene-based epoxy resins were allowed to react with the acid anhydrides as in Synthetic Example 1 to yield Compound 6 (m/n=50/50). The reaction with the acid anhydrides was confirmed by infrared spectrometry. The compound showed an inherent viscosity of 0.3 dl/g ($\eta_{inh}$=0.3).

Synthetic Example 7

The epoxy acrylates prepared as in Synthetic Example 1 except using 181 g of sulfone-based epoxy resins (epoxy equivalent 181) in place of the bisphenolfluorene-based epoxy resins were allowed to react with the acid anhydrides as in Synthetic Example t to yield Compound 7 (m/n=50/50). The reaction with the acid anhydrides was confirmed by infrared spectrometry. The compound showed an inherent viscosity of 0.3 dl/g ($\eta_{inh}$=0.3).

Synthetic Example 8

The epoxy acrylates prepared as in Synthetic Example 1 except using 221 g of hexafluoropropane-based epoxy resins (epoxy equivalent 221) in place of the bisphenolfluorene-based epoxy resins were allowed to react with the acid anhydrides as in Synthetic Example 1 to yield Compound 8 (m/n=50/50). The reaction with the acid anhydrides was confirmed by infrared spectrometry. The compound showed an inherent viscosity of 0.4 dl/g ($\eta_{inh}$=0.4).

Synthetic Example 9

The epoxy acrylates prepared as in Synthetic Example 1 except using 163 g of dimethylsilane-based epoxy resins (epoxy equivalent 163) in place of the bisphenolfluorene-based epoxy resins were allowed to react with the acid anhydrides as in Synthetic Example 1 to yield Compound 9 (m/n=50/50). The reaction with the acid anhydrides was confirmed by infrared spectrometry. The compound showed an inherent viscosity of 0.2 dl/g ($\eta_{inh}$=0.2).

Synthetic Example 10

The epoxy acrylates prepared as in Synthetic Example 1 except using 156 g of diphenylmethane-based epoxy resins (epoxy equivalent 156) in place of the bisphenolfluorene-based epoxy resins were allowed to react with the acid anhydrides as in Synthetic Example 1 to yield Compound 10 (m/n=50/50). The reaction with the acid anhydrides was confirmed by infrared spectrometry. The compound showed an inherent viscosity of 0.4 dl/g ($\eta_{inh}$=0.4).

Synthetic Example 11

The epoxy acrylates prepared as in Synthetic Example 1 except using 170 g of diphenylpropane-based epoxy resins (epoxy equivalent 170) in place of the bisphenolfluorene-based epoxy resins were allowed to react with the acid anhydrides as in Synthetic Example 1 to yield Compound 11 (m/n=50/50). The reaction with the acid anhydrides was confirmed by infrared spectrometry. The compound showed an inherent viscosity of 0.4 dl/g ($\eta_{inh}$=0.4).

Synthetic Example 12

The epoxy acrylates prepared as in Synthetic Example 1 except using 157 g of diphenyl ether-based epoxy resins (epoxy equivalent 157) in place of the bisphenolfluorene-based epoxy resins were allowed to react with the acid anhydrides as in Synthetic Example 1 to yield Compound 12 (m/n=50/50). The reaction with the acid anhydrides was confirmed by infrared spectrometry. The compound showed an inherent viscosity of 0.3 dl/g ($\eta_{inh}$=0.3).

Synthetic Example 13

A solution of 303 g of the bisphenolfluorene-based epoxy acrylates prepared in Synthetic Example 1 in 2 kg of cellosolve acetate was mixed with 76.0 g of 1,2,3,6-tetrahydrophthalic anhydride and 1 g of tetraethylammonium bromide and the mixture was gradually heated up and kept at 95° to 100° C. for 4 hours to yield Compound 13 (m/n=100/0). The reaction with the acid anhydride was confirmed by infrared spectrometry. The compound showed an inherent viscosity of 0.15 dl/g ($\eta_{inh}$=0.15).

Synthetic Example 14

The procedure in Synthetic Example 13 was followed except using 153 g of biphenyl-based epoxy resins (epoxy equivalent 153) in place of the bisphenolfluorene-based epoxy resins of Synthetic Example 1 to yield Compound 14 (m/n=100/0). The reaction with the acid anhydride was confirmed by infrared spectrometry. The compound showed an inherent viscosity of 0.16 dl/g ($\eta_{inh}$=0.16).

The synthesis of the component C or ortho spiroesters is described in Synthetic Examples 15 to 19.

Synthetic Example 15

The synthesis was carried out as in Example 1 to yield cardo adducts of γ-butyrolactone (Compound 15).

Synthetic Example 16

The synthesis was carried out as in Example 2 with substitution of ε-caprolactone for γ-butyrolactone to yield Compound 16.

Synthetic Example 17

The synthesis was carried out as in Synthetic Example 15 with substitution of epoxy resins based on bisphenol A diglycidyl ether (Epikote 828 with epoxy equivalent 190 manufactured by Yuka Shell Epoxy K.K.) for the bisphenolfluorene-based epoxy resins to yield Compound 17.

Synthetic Example 18

The synthesis was carried out as in Synthetic Example 15 with substitution of epoxy resins based on cresol novplak diglycidyl ether for the bisphenolfluorene-based epoxy resins and ε-caprolactone for γ-butyrolactone to yield Compound 18.

Synthetic Example 19

The synthesis was carried out as in Synthetic Example 15 with substitution of alicyclic epoxy resins (2021P manufactured by Daicel Chemical Industries, Ltd. ) for the bisphenolfluorene-based epoxy resins and ε-caprolactone for γ-butyrolactone to yield Compound 19.

Synthetic Example 20

A solution of 230 g of the bisphenolfluorene-based epoxy acrylates prepared in Synthetic Example 1 in 258 g of cellosolve acetate was mixed with 18.24 g of trimellitic anhydride, 55.9 g of biphenyltetracarboxylic acid dianhydride and 1 g of tetraethylammonium bromide and the mixture was gradually heated up and kept at 110° to 115° C. for 2 hours to yield Compound 20 (m/n=34/66). The reaction with the acid anhydrides was confirmed by infrared spectrometry. The compound showed an inherent viscosity of 0.20 dl/g ($\eta_{inh}$=0.20) and an acid value of 100.

EXAMPLES 11 TO 33 AND COMPARATIVE EXAMPLES 3 AND 4

Resist solutions were prepared from the components A and B obtained in the aforementioned Synthetic Examples 1 to 14 and 20, the component C obtained in the aforementioned Synthetic Examples 15 to 19, and, as needed, photopolymerizable acrylic monomers and oligomers and organic solvents according to the formulation (by weight) shown in Table 2.

TABLE 2

| Example No. | 11 | | 12 | | 13 | | 14 | | 15 | |
|---|---|---|---|---|---|---|---|---|---|---|
| Compound No. and amount added / Compound No. Amount added | 1 20 | 15 4 | 1 20 | 16 4 | 1 20 | 17 4 | 1 20 | 18 4 | 1 20 | 19 4 |
| Michler's ketone*[1] | 0.1 | | 0.1 | | 0.1 | | 0.1 | | 0.1 | |
| Irgacure 907*[2] | 0.6 | | 0.6 | | 0.6 | | 0.6 | | 0.6 | |
| Cellosolve acetate | 75.3 | | 75.3 | | 75.3 | | 75.3 | | 75.3 | |

| Example No. | 16 | | 17 | | 18 | | 19 | | 20 | |
|---|---|---|---|---|---|---|---|---|---|---|
| Compound No. and amount added / Compound No. Amount added | 2 20 | 15 4 | 5 20 | 15 4 | 6 20 | 15 4 | 7 20 | 15 4 | 8 20 | 15 4 |
| Michler's ketone*[1] | 0.1 | | 0.1 | | 0.1 | | 0.1 | | 0.1 | |
| Irgacure 907*[2] | 0.6 | | 0.6 | | 0.6 | | 0.6 | | 0.6 | |
| Cellosolve acetate | 75.3 | | 75.3 | | 75.3 | | 75.3 | | 75.3 | |

| Example No. | 21 | | 22 | | 23 | | 24 | | 25 | |
|---|---|---|---|---|---|---|---|---|---|---|
| Compound No. and amount added / Compound No. Amount added | 9 20 | 15 4 | 10 20 | 15 4 | 11 20 | 15 4 | 12 20 | 15 4 | 5 20 | 17 4 |
| Michler's ketone*[1] | 0.1 | | 0.1 | | 0.1 | | 0.1 | | 0.1 | |
| Irgacure 907*[2] | 0.6 | | 0.6 | | 0.6 | | 0.6 | | 0.6 | |
| Cellosolve acetate | 75.3 | | 75.3 | | 75.3 | | 75.3 | | 75.3 | |

| Example No. | 26 | | 27 | | 28 | | 29 | | 30 | |
|---|---|---|---|---|---|---|---|---|---|---|
| Compound No. and amount added / Compound No. Amount added | 5 20 | 18 4 | 1 20 | 15 4.4 | 5 16 | 15 12 | 3 20 | 16 8 | 4 20 | 16 8 |
| Michler's ketone*[1] | 0.1 | | 0.2 | | 0.1 | | 0.1 | | 0.1 | |
| Irgacure 907*[2] | 0.6 | | 1.2 | | 0.6 | | 1.0 | | 1.0 | |
| Cellosolve acetate | 75.3 | | 65.6 | | 71.3 | | 70.9 | | 70.9 | |
| Other additive*[3] | — | | ①8.6 | | — | | — | | — | |

| Example No. | 31 | | 32 | | 33 | | Comparative example 3 | | Comparative example 4 | |
|---|---|---|---|---|---|---|---|---|---|---|
| Compound No. and amount added / Compound No. Amount added | 13 20 | 15 8 | 14 20 | 16 8 | 20 20 | 15 4.4 | 1 20 | 0 0 | 1 20 | 0 0 |
| Michler's ketone*[1] | 0.1 | | 0.1 | | 0.2 | | 0.1 | | 0.1 | |
| Irgacure 907*[2] | 0.6 | | 0.6 | | 1.2 | | 0.6 | | 0.6 | |
| Cellosolve acetate | 71.3 | | 71.3 | | 65.6 | | 76.3 | | 79.3 | |
| Other additive*[3] | — | | — | | ①8.6 | | ②3 | | — | |

(Notes)
*[1] 4,4'-Dimethylaminobenzophenone
*[2] 2-Methyl-1-(4-methylthiophenyl)-2-morpholinopropan-2-one (product of Ciba-Geigy)
*[3] ①: Dipentaerythritol hexaacrylate (DPHA, product of Nippon Kayaku Co., Ltd.) ②: 3,3',5,5'-Tetramethyl-4,4'-di(2,3-epoxypropoxy)biphenyl (YX-4000H, product of Yuka Shell Epoxy K.K.)

Each of the resist solutions (Examples 11 to 28 and 33) was applied to a degreased 1.2 mm-thick glass plate to a thickness of approximately 2 μm and dried, and the resulting film was placed in close contact with a photomask and irradiated with ultraviolet light of a wavelength of 365 nm and an illuminance of 10 mW/cm² generated by a 500-W high-pressure mercury lamp for 20 seconds. After exposure to the ultraviolet light, the film was developed with a 1% by weight aqueous solution of sodium carbonate at 25° C. for 30 seconds to remove the unexposed portion. Thereafter, the film was dried in a hot-air dryer at 200° C. for 30 minutes. The surface of the film was very smooth.

The sample thus obtained was tested for its drying characteristics of film, developability with an aqueous alkaline solution, sensitivity to exposure to light, hardness of film, adhesion of film to substrate, decrease in film thickness during curing, heat resistance and chemical resistance. The results are shown in Table 3.

The sample was further tested for its adhesion to Nesa glass (glass metallized with ITO). The results are shown in Table 3.

decrease in film thickness than the samples of the aforementioned examples.

In Comparative Example 4 which is free of the component C, there remained a problem regarding the alkali resistance after curing by heat.

The aforementioned properties were determined under the following conditions.

(1) Drying characteristics of film

The drying characteristics of film were determined according to JIS-5400 and ranked as follows.

○: No tack is observed.

Δ: Slight tack is observed.

TABLE 3

| Example No. | 11 | 12 | 13 | 14 | 15 | 16 | 17 | 18 | 19 | 20 | 21 | 22 | 23 |
|---|---|---|---|---|---|---|---|---|---|---|---|---|---|
| Drying characteristics of film | ○ | ○ | ○ | ○ | ○ | ○ | ○ | ○ | ○ | ○ | ○ | ○ | ○ |
| Developability | ○ | ○ | ○ | ○ | ○ | ○ | ○ | ○ | ○ | ○ | ○ | ○ | ○ |
| Sensitivity to exposure to light | 8 | 8 | 8 | 8 | 8 | 8 | 9 | 8 | 9 | 9 | 9 | 9 | 9 |
| Hardness of film | 4H | 4H | 4H | 4H | 4H | 4H | 5H | 4H | 5H | 4H | 4H | 5H | 5H |
| Adhesion to glass | ○ | ○ | ○ | ○ | ○ | ○ | ○ | ○ | ○ | ○ | ○ | ○ | ○ |
| ITO | ○ | ○ | ○ | ○ | ○ | ○ | ○ | ○ | ○ | ○ | ○ | ○ | ○ |
| Decrease in film thickness | 2 | 3 | 4 | 2 | 3 | 3 | 3 | 2 | 2 | 3 | 4 | 3 | 3 |
| Heat resistance | ○ | ○ | ○ | ○ | ○ | ○ | ○ | ○ | ○ | ○ | ○ | ○ | ○ |
| Chemical resistance | ○ | ○ | ○ | ○ | ○ | ○ | ○ | ○ | ○ | ○ | ○ | ○ | ○ |
| Transparency | ○ | ○ | ○ | ○ | ○ | ○ | ○ | ○ | ○ | ○ | ○ | ○ | ○ |

| Example No. | 24 | 25 | 26 | 27 | 28 | 29 | 30 | 31 | 32 | 33 | Comparative Example 3 | Comparative Example 4 |
|---|---|---|---|---|---|---|---|---|---|---|---|---|
| Drying characteristics of film | ○ | ○ | ○ | ○ | ○ | ○ | ○ | ○ | ○ | ○ | ○ | ○ |
| Developability | ○ | ○ | ○ | ○ | ○ | — | — | — | — | ○ | ○ | Δ |
| Sensitivity to exposure to light | 9 | 9 | 9 | 8 | 9 | 8 | 9 | 9 | 9 | 8 | 8 | 8 |
| Hardness of film | 5H | 4H | 5H | 5H | 4H | 4H | 5H | 4H | 4H | 4H | 4H | 4H |
| Adhesion to glass | ○ | ○ | ○ | ○ | ○ | ○ | ○ | ○ | ○ | ○ | ○ | ○ |
| ITO | ○ | ○ | ○ | ○ | ○ | ○ | ○ | ○ | ○ | ○ | ○ | ○ |
| Decrease in film thickness | 3 | 4 | 3 | 4 | 1 | 4 | 3 | 4 | 4 | 3 | 10 | 12 |
| Heat resistance | ○ | ○ | ○ | ○ | ○ | ○ | ○ | ○ | ○ | ○ | ○ | ○ |
| Chemical resistance | ○ | ○ | ○ | ○ | ○ | ○ | ○ | ○ | ○ | ○ | ○ | X[a] |
| Transparency | ○ | ○ | ○ | ○ | ○ | ○ | ○ | ○ | ○ | ○ | ○ | X[a] |

(Note)
[a]: At the time of alkali resistance test

As is apparent from Table 3, each of the samples obtained in Examples 11 to 28 and 33 satisfied the target properties.

Each of the resist solutions (Examples 29 to 32) was applied by a screen printer to a degreased 1.2 mm-thick glass plate to a thickness of approximately 2 μm, dried, irradiated with ultraviolet light with a wavelength of 365 nm and an illuminance of 10 mW/cm$^2$ generated by a 500-W high-pressure mercury lamp for 20 seconds, and dried in a hot-air dryer at 150° C. for 60 minutes.

The resulting film was tested as above (except for the developability of film) and was found to satisfy the target properties in any of Examples 29 to 32.

Moreover, the photosensitive resin compositions of this invention can provide cured products on ITO such as Nesa glass with excellent heat resistance, transparency, adhesive properties, hardness, solvent resistance, alkali resistance and smoothness and they are useful as spacer materials for touch panels.

On the other hand, in Comparative Example 3, epoxy compounds were substituted for the ortho spiroesters in the formulation and the sample here was found to show a greater x: Marked tack is observed.

(2) Developability with aqueous alkaline solution

Development was performed by immersion in a 1% by weight aqueous solution of sodium carbonate for 30 seconds. The sample after development was visually observed under 40-fold magnification for the condition of residual resins and the results were evaluated by the following ranking.

○: Good developability (no resist remaining on the glass).

x: Poor developability (a little resist remaining on the glass).

(3) Sensitivity to exposure to light

The film was placed in close contact with Kodak Step Tablet No. 2 (a nagative film with 21 steps, differing in optical density by 0.15 between the consecutive steps, manufactured by Eastman Kodak Co.) and exposed to light in an amount of 200 mj./cm$^2$ with the aid of a 500-W high-pressure mercury lamp. The film was tested for the step difference of the step tablet after development with the aforementioned weakly alkaline aqueous solution. According to this method, the higher the sensitivity, the greater the number of residual steps becomes.

(4) Hardness of film

After exposure and development, the film was heated at 200° C. for 30 minutes and tested for its hardness according to JIS-K5400 with the aid of a pencil hardness tester. The hardest pencil which left the film unscratched under a load of 1 kg was taken as the hardness of the film. The pencil used was "Mitsubishi Hi-Uni."

(5) Adhesion to substrate

After exposure and development, the film was heated at 200° C. for 30 minutes, cross-cut into a grid with at least 100 squares, a pressure-sensitive tape was applied over the grid and peeled off and the condition of the peeled surface was visually observed and evaluated by the following ranking.

○: No peeling is observed.

x: Peeling, however slight, is observed.

(6) Decrease in film thickness

The percentage decrease in film thickness was defined as 100 {1-(D/d)} where d is the film thickness after exposure and development and D is the film thickness after heating at 200° C. for 30 minutes.

(7) Heat resistance

After exposure and development, the film was heated at 200° C. for 30 minutes and then placed in an oven at 250° C. for 3 hours and the condition of the film was evaluated by the following ranking.

○: No abnormality is observed.

x: Cracking, peeling or discoloration is observed.

(8) Chemical resistance

After exposure and development, the film was heated at 200° C. for 30 minutes and then immersed in the following chemicals under the following conditions and the appearance and adhesion after the immersion were evaluated.

Acid resistance: in 5% HCl for 24 hours

Alkali resistance: in 5% NaOH for 24 hours in 4% KOH at 50° C. for 10 minutes in 1% NaOH at 80° C. for 5 minutes Solvent resistance: in NMP at 40° C. for 10 minutes in NMP at 80° C. for 5 minutes (NMP: N-methylpyrrolidone)

(9) Transparency

The coated glass plate was tested for absorbance in the wavelength range of 400 to 800 nm before and after the tests for heat and chemical resistance with the uncoated glass plate as reference.

○: 95% or more in the whole range x: less than 95% in the whole range

EXAMPLE 34

A varnish with the composition shown in Example 27 was mixed with a pigment which had been dispersed in an organic solvent in advance and the mixture was dispersed to yield an ink for color filter. The pigment used was CF Color Red EX-274, CF Color Green EX-276, CF Color Blue EX-275 and CF Color Black EX-277 (manufactured by Mikuni Color Works Ltd.). Each pigment was dispersed to a particle diameter of 0.3 μm. The composition by weight of inks is shown in Table 4.

TABLE 4

| Kind of ink | Composition of ink (parts by weight) | | |
|---|---|---|---|
| | Resin composition ① | Pigment | Solvent |
| RED | 15 | 8 | 77 |
| GREEN | 15 | 8 | 77 |
| BLUE | 17 | 6 | 77 |
| BLACK | 15 | 10 | 75 |

A glass substrate was cleaned successively with a neutral detergent, water and isopropyl alcohol.flon and used as transparent substrate. The substrate was spin-coated with each ink, dried at 80° C., placed in close contact with a photomask and irradiated with ultraviolet light of a wavelength of 365 nm and an illuminance of 10 mW/cm$^2$ generated by a 500-W high-pressure mercury lamp for 20 seconds. After exposure, the film was developed with a 1% by weight aqueous solution of sodium carbonate at 25° C. for 30 seconds to remove the unexposed portion of the film. Thereafter, the film was heated in a hot-air dryer at 200° C. for 30 minutes. The film thickness after the heating was 2±0.1 μm for red, green, blue and black matrixes.

Comparative Example 5

A mixture of 6 parts by weight of poly(vinyl alcohol) (EG-30 manufactured by The Nippon Synthetic Chemical Industry Co., Ltd.), 0.5 part by weight of ammonium dichromate, 0.3 part by weight of chrome alum and 93.2 parts by weight of water as a photosensitive dyeing base and Red 24P, Green 1P or Blue 5C as dye were used to perform dyeing under the conditions shown in Table 5.

Prebake was effected at 60° C. for 10 minutes and the dyes were applied in the order of R, G and B and the thickness of the pixel was 1.5±0.2 μm for each of the R, G and B.

TABLE 5

| | Spin speed · time | Dose | Dyeing conditioin | |
|---|---|---|---|---|
| | (rpm × 10 secons) | (mj/cm$^2$) | Temperature:°C. | pH |
| RED | 500 | 100 | 60 | 4.0 |
| GREEN | 500 | 100 | 60 | 4.5 |
| BLUE | 500 | 100 | 60 | 5.5 |

The color filters prepared in the aforementioned Example 34 and Comparative Example 5 were tested for their light resistance in a xenon arc fadeometer. The values of ΔE (color difference) by $L_{ab}$ after 1,000 hours are shown in Table 6.

It is apparent that the color filter of Example 34 shows a distinctly smaller value of ΔE and greater reliability in light resistance than that of Comparative Example 5.

TABLE 6

| | RED | GREEN | BLUE |
|---|---|---|---|
| Example 34 | 1.5 | 1.2 | 1.0 |
| Comparative example 3 | 5.5 | 7.0 | 4.8 |

Comparative Example 6

A color filter was prepared as in Comparative Example 5 using Color Mosaic (R, G and B manufactured by Fuji Hunt Co., Ltd.).

Prebake was effected at 90° C. for 5 minutes and the specified developer solution was used in development. The thickness of the pixel thus prepared was 2±0.1 μm for each of R, G and B.

The color filters of aforementioned Example 34 and Comparative Example 6 were tested for their heat resistance (at 280° C. for 1 hour) and the decreases in the peak value of spectral transmittance and in the film thickness were determined. The results are shown in Table 7.

TABLE 7

|  | RED | GREEN | BLUE |
|---|---|---|---|
| Reduction in peak value of spectral transmittance (%) | | | |
| Example 34 | 3.0 | 2.7 | 3.5 |
| Comparative example 4 | 4.5 | 5.5 | 7.6 |
| Decrease in film thickness (%) | | | |
| Example 34 | 7.1 | 8.8 | 6.4 |
| Comparative example 4 | 7.2 | 25.0 | 20.0 |

EXAMPLE 35

The resin compositions prepared in Examples 11 to 32 were tested for their applicability to color filter substrates. The following test method was used.

A color filter base was prepared as in Comparative Example 6, spin-coated with the aforementioned resin compositions, dried at 80° C. for 10 minutes, placed in close contact with a photomask, and irradiated with ultraviolet light of a wavelength of 365 nm and an illuminance of 10 mW/cm$^2$ generated by a 500-W high-pressure mercury lamp for 20 seconds.

After exposure, the film was developed with a 1% by weight aqueous solution of sodium carbonate at 25° C. for 30 seconds to remove the unexposed portion. Thereafter, the film was dried in a hot-air dryer at 200° C. for 30 minutes. The surface of the film was very smooth.

The color filter provided with a protective film thus prepared was metallized with indium tin oxide (ITO) in the usual manner and subjected to patterning by photolithography.

Detailed observation of this color filter with the ITO patterns under an optical microscope revealed the absence of wrinkles and cracks in the color filter and protective film and good adhesion of the color filter and protective film.

The results described above indicate that the photosensitive resin compositions of this invention can provide cured products, films and color filters with excellent heat resistance, transparency, adhesive properties, hardness, solvent resistance, alkali resistance and smoothness.

EXAMPLES 36 TO 58 AND COMPARATIVE EXAMPLES 7 AND 8

Solutions are prepared by mixing the components A and B obtained in the aforementioned Synthetic Examples 1 to 14 and 20, the component C obtained in the aforementioned Synthetic Examples 15 to 19, and, as needed, thermally polymerizable acrylic monomers and oligomers and solvents according to the formulation by weight shown in Table 8.

TABLE 8

| Example No. | 36 | | 37 | | 38 | | 39 | | 40 | |
|---|---|---|---|---|---|---|---|---|---|---|
| Com- pound No. and amount added | Com- pound No. Amount added | 1 20 | 15 4 | 1 20 | 16 4 | 1 20 | 17 4 | 1 20 | 18 4 | 1 20 | 18 4 |
| Benzoyl peroxide | | 0.7 | | 0.7 | | 0.7 | | 0.7 | | 0.7 | |
| Cellosolve acetate | | 75.3 | | 75.3 | | 75.3 | | 75.3 | | 75.3 | |

| Example No. | 41 | | 42 | | 43 | | 44 | | 45 | |
|---|---|---|---|---|---|---|---|---|---|---|
| Com- pound No. and amount added | Com- pound No. Amount added | 2 20 | 15 4 | 5 20 | 15 4 | 6 20 | 17 4 | 7 20 | 15 4 | 8 20 | 15 4 |
| Benzoyl peroxide | | 0.7 | | 0.7 | | 0.7 | | 0.7 | | 0.7 | |
| Cellosolve acetate | | 75.3 | | 75.3 | | 75.3 | | 75.3 | | 75.3 | |

| Example No. | 46 | | 47 | | 48 | | 49 | | 50 | |
|---|---|---|---|---|---|---|---|---|---|---|
| Com- pound No. and amount added | Com- pound No. Amount added | 9 20 | 15 4 | 10 20 | 15 4 | 11 20 | 17 4 | 12 20 | 15 4 | 5 20 | 17 4 |
| Benzoyl peroxide | | 0.7 | | 0.7 | | 0.7 | | 0.7 | | 0.7 | |
| Cellosolve acetate | | 75.3 | | 75.3 | | 75.3 | | 75.3 | | 75.3 | |

| Example No. | 51 | | 52 | | 53 | | 54 | | 55 | |
|---|---|---|---|---|---|---|---|---|---|---|
| Com- pound No. and amount added | Com- pound No. Amount added | 5 20 | 18 4 | 1 20 | 15 4.4 | 5 16 | 15 12 | 3 20 | 16 8 | 4 20 | 16 8 |
| Benzoyl peroxide | | 0.7 | | 1.4 | | 0.6 | | 0.7 | | 1.0 | |
| 2MA-OK*[1] | | — | | — | | 0.13 | | — | | 0.1 | |
| Cellosolve acetate | | 75.3 | | 65.6 | | 71.3 | | 70.9 | | 70.9 | |
| Other additive*[2] | | — | | ①8.6 | | — | | — | | — | |

| Example No. | 56 | | 57 | | 58 | | Comparative example 7 | | Comparative example 8 | |
|---|---|---|---|---|---|---|---|---|---|---|
| Com- pound No. and amount added | Com- pound No. Amount added | 13 20 | 15 8 | 14 20 | 16 8 | 20 20 | 15 4.4 | 1 20 | — — | 1 20 | — — |
| Benzoyl peroxide | | 0.7 | | 0.6 | | 1.4 | | 0.6 | | 0.7 | |
| 2MA-OK*[1] | | — | | 0.1 | | 0.05 | | 0.1 | | — | |
| Cellosolve acetate | | 71.3 | | 71.3 | | 65.6 | | 76.3 | | 79.3 | |
| Other additive*[2] | | — | | — | | ①8.6 | | ②3 | | — | |

(Notes)
*[1]: 2,4-Diamino-6-(2'-methylimidazolyl-1')ethyl-5-triazine-isocyanuric acid adduct (product of Shikoku Chemicals Corporation)
*[2]①: Dipentaerythritol hexaacrylate (DPHA, product of Nippon Kayaku Co., Ltd.) ②: 3,3',5,5'-Tetramethyl-4,4'-di(2,3-epoxypropoxy)biphenyl (YX-4000H, product of Yuka Shell Epoxy K.K.)

Each of the solutions thus prepared was applied to a degreased 1.2 mm-thick glass plate to a thickness of approximately 2 μm, dried and then heated in a hot-air dryer at 200° C. for 60 minutes to give a film with an extremely smooth surface.

The samples thus obtained above in the same manner as earlier except foregoing the steps of exposure and development were tested for drying characteristics of film, hardness of film, adhesion to substrate, decrease in film thickness during curing, heat resistance and chemical resistance. The results are shown in Table 9.

The adhesion to Nesa glass (glass metallized with ITO) was also evaluated and the results are shown in Table 9.

TABLE 9

| Example No. | 36 | 37 | 38 | 39 | 40 | 41 | 42 | 43 | 44 | 45 | 46 | 47 | 48 |
|---|---|---|---|---|---|---|---|---|---|---|---|---|---|
| Drying characteristics of film | O | O | O | O | O | O | O | O | O | O | O | O | O |
| Hardness of film | 4H | 4H | 4H | 4H | 4H | 4H | 5H | 4H | 5H | 4H | 4H | 5H | 5H |
| Adhesion to glass | O | O | O | O | O | O | O | O | O | O | O | O | O |
| ITO | O | O | O | O | O | O | O | O | O | O | O | O | O |
| Decrease in film thickness | 5 | 6 | 7 | 5 | 7 | 5 | 6 | 5 | 5 | 5 | 7 | 6 | 6 |
| Heat resistance | O | O | O | O | O | O | O | O | O | O | O | O | O |
| Chemical resistance | O | O | O | O | O | O | O | O | O | O | O | O | O |
| Transparency | O | O | O | O | O | O | O | O | O | O | O | O | O |

| | | | | | | | | | | | Comparative Example | |
|---|---|---|---|---|---|---|---|---|---|---|---|---|
| Example No. | 49 | 50 | 51 | 52 | 53 | 54 | 55 | 56 | 57 | 58 | 7 | 8 |
| Drying characteristics of film | O | O | O | O | O | O | O | O | O | O | O | O |
| Hardness of film | 5H | 4H | 5H | 5H | 4H | 4H | 5H | 4H | 4H | 4H | 4H | 4H |
| Adhesion to glass | O | O | O | O | O | O | O | O | O | O | O | O |
| ITO | O | O | O | O | O | O | O | O | O | O | O | O |
| Decrease in film thickness | 6 | 7 | 5 | 7 | 3 | 7 | 6 | 8 | 8 | 6 | 17 | 18 |
| Heat resistance | O | O | O | O | O | O | O | O | O | O | O | O |
| Chemical resistance | O | O | O | O | O | O | O | O | O | O | O | X[a] |
| Transparency | O | O | O | O | O | O | O | O | O | O | O | X[a] |

(Note)
[a]: At the time of alkali resistance test

As is apparent from Table 9, the samples of Examples 36 to 53 produced good results.

The resist solutions (Examples 54 to 57) were each applied by a screen printer to a degreased 1.2 mm-thick glass plate to a thickness of approximately 2 μm, dried, irradiated with ultraviolet light of a wavelength of 365 nm and an illuminance of 10 mW/cm² generated by a 500-W high-pressure mercury lamp for 20 seconds, and heated in a hot-air dryer at 200° C. for 60 minutes.

The films thus obtained were evaluated as above (excepting the developability of film) and the samples of Examples 54 to 57 were all found to attain the target properties.

Moreover, the heat-curable resin compositions of this invention cure on ITO such as Nesa glass with excellent heat resistance, transparency, adhesion, hardness, solvent resistance, alkali resistance and smoothness and they are useful as spacer materials for touch panels.

On the other hand, in Comparative Example 7 where epoxy compounds were substituted for the ortho spiroesters in the formulation, the decrease in film thickness was found greater than in the aforementioned Examples.

In Comparative Example 8 which is free of the component C, there was a problem in the alkali resistance after heat curing.

EXAMPLE 59

A varnish with the composition shown in Example 53 was mixed with a pigment which had been dispersed in an organic solvent in advance and the mixture was dispersed to yield an ink for color filter. The pigment used was CF Color Red EX-274, CF Color Green EX-276, CR Color Blue EX-275 and CF Color Black 277 (manufactured by Mikuni Color Works Ltd.). Each pigment was dispersed to a particle diameter of 0.3 μm. The composition by weight of inks was made the same as in Example 34 shown in Table 4.

A glass substrate was cleaned successively with a neutral detergent, water and isopropyl alcohol.flon and used as transparent substrate. The substrate was spin-coated with each ink, dried at 80° C., placed in close contact with a photomask and irradiated with ultraviolet light of a wavelength of 365 nm and an illuminance of 10 mW/cm² generated by a 500-W high-pressure mercury lamp for 20 seconds. After exposure, the film was developed with a 1% by weight aqueous solution of sodium carbonate at 25° C. for 30 seconds to remove the unexposed portion of the film. Thereafter, the film was heated in a hot-air dryer at 200° C. for 30 minutes. The film thickness after the heating was 2±0.1 μm for red, green, blue and black matrixes.

Comparative Example 9

A mixture of 6 parts by weight of poly(vinyl alcohol) (EG-30 manufactured by The Nippon Synthetic Chemical Industry Co., Ltd.), 0.5 part by weight of ammonium dichromate, 0.3 part by weight of chrome alum and 93.2 parts by weight of water as a photosensitive dyeing base and Red 24P, Green 1P or Blue 5C as dye were used to perform dyeing under the conditions shown in Table 5.

Prebake was effected at 60° C. for 10 minutes and the dyes were applied in the order of R, G and B and the thickness of the pixel was 1.5±0.2 μm for each of the R, G and B.

The color filters prepared in the aforementioned Example 59 and Comparative Example 9 were tested for their light resistance in a xenon arc fadeometer. The values of ΔE (color difference) by $L_{ab}$ after 1,000 hours were the same as in Example 34 and Comparative Example 3 shown in Table 6, respectively.

It is apparent that the color filter of Example 34 shows a distinctly smaller value of ΔE and greater reliability in light resistance than that of Comparative Example 9.

Comparative Example 10

A color filter was prepared as in Comparative Example 9 using Color Mosaic (R, G and B manufactured by Fuji Hunt Co., Ltd.).

Prebake was effected at 90° C. for 5 minutes and the specified developer solution was used in development. The thickness of the pixel thus prepared was 2±0.1 μm for each of R, G and B.

The color filters of aforementioned Example 59 and Comparative Example 10 were tested for their heat resistance (at 280° C. for 1 hour) and the reductions in the peak value of spectral transmittance and in the film thickness were determined. The results were the same as in Example 34 and Comparative Example 6 shown in Table 7.

EXAMPLE 60

The resin compositions prepared in Examples 36 to 58 were tested for their applicability to color filter substrates. The following test method was used.

A color filter base was prepared as in Comparative Example 10, spin-coated with the aforementioned resin compositions, dried at 80° C. for 10 minutes, placed in close contact with a photomask, and irradiated with ultraviolet light of a wavelength of 365 nm and an illuminance of 10 mW/cm$^2$ generated by a 500-W high-pressure mercury lamp for 20 seconds.

After exposure, the film was developed with a 1% by weight aqueous solution of sodium carbonate at 25° C. for 30 seconds to remove the unexposed portion. Thereafter, the film was dried in a hot-air dryer at 200° C. for 30 minutes. The surface of the film was very smooth.

The color filter provided with a protective film thus prepared was metallized with indium tin oxide (ITO) in the usual manner and subjected to patterning by photolithography.

Detailed observation of this color filter with the ITO patterns under an optical microscope revealed the absence of wrinkles and cracks in the color filter and protective film and good adhesion of the color filter and protective film.

The results described above indicate that the photosensitive resin compositions of this invention can provide cured products, films and color filters with excellent heat resistance, transparency, adhesion, hardness, solvent resistance, alkali resistance and smoothness.

Industrial Applicability

The ortho spiroesters of this invention show large expansion in volume during curing and hence they enable the preparation of resin compositions which show small shrinkage in volume as a whole during curing. Moreover, they can provide resin compositions of improved heat resistance by incorporating them into resin compositions that contain epoxy resins and are intended for low shrinkage during curing. In consequence, they are able to lower the internal stress which develops from volume shrinkage during curing and they are particularly useful as molding materials, encapsulants and adhesives requiring dimensional accuracy. Moreover, the resin compositions containing the ortho spiroesters of this invention cure with excellent heat resistance and are useful for applications requiring high heat resistance.

The photosensitive or heat-curable resin compositions of low curing shrinkage of this invention form tack-free films when their solutions are dried and the films cure with relatively low shrinkage. They are thus able to provide accurate resist patterns on substrates and cure with excellent adhesion, transparency, heat resistance, resistance to acids, alkalis and solvents, smoothness and surface hardness compared with the conventional materials.

In consequence, the compositions in question are suitable for providing surface protective layers on which transparent electrodes such as ITO can be formed. In addition, their films are extremely smooth and transparent and capable of producing clear images when used as materials for color filters.

In the event that the photosensitive or heat-curable resin compositions of low curing shrinkage are used as spacer materials for touch panels, they show a smaller decrease in the film thickness and in the pattern width in the course of heat treatment and provide spacers of excellent surface hardness and transparency. Thus, the compositions as spacer materials offer such advantages as reduction in size of basic key matrixes, possibility of input by pen, flexibility in the number and arrangement of keys for touch panels and ability to cope with a variety of input information.

Furthermore, the resin compositions of this invention form films with good adhesion to substrates and chemical resistance and are applicable with high reliability to a wide variety of end uses such as interlayer insulating materials related to printed circuit boards, optical materials, adhesives, coatings and screen-printing inks.

What is claimed is:

1. An ortho spiroester represented by the following general formula (1)

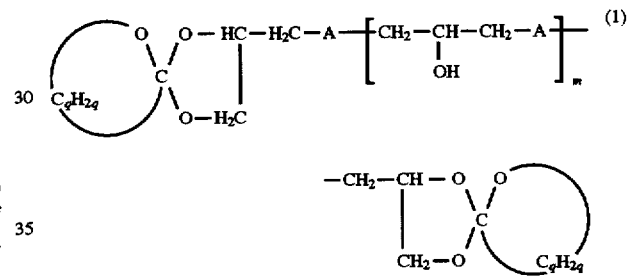

wherein A is with R designating hydrogen or a lower alkyl group, m is 0 to 10 and q is an integer from 2 to 10.

2. The ortho spiroester as claimed in claim 1, wherein R is hydrogen.

3. The ortho spiroester as claimed in claim 1, wherein m is 0 to 3.

4. The ortho spiroester as claimed in claim 1, wherein m is 1 to 10.

5. The ortho spiroester as claimed in claim 1, wherein q is 2–5.

6. The ortho spiroester as claimed in claim 1, wherein R is selected from the group consisting of hydrogen, methyl, ethyl, and isopropyl.

* * * * *